(12) United States Patent
Dreyfuss et al.

(10) Patent No.: US 8,993,741 B2
(45) Date of Patent: Mar. 31, 2015

(54) SMNDELTA7 DEGRON: NOVEL COMPOSITIONS AND METHODS OF USE

(75) Inventors: Gideon Dreyfuss, Wynnewood, PA (US); Sungchan Cho, Chungbuk (KR)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 22 days.

(21) Appl. No.: 13/510,149

(22) PCT Filed: Nov. 17, 2010

(86) PCT No.: PCT/US2010/056985
§ 371 (c)(1),
(2), (4) Date: Aug. 6, 2012

(87) PCT Pub. No.: WO2011/062962
PCT Pub. Date: May 26, 2011

(65) Prior Publication Data
US 2012/0322852 A1    Dec. 20, 2012

Related U.S. Application Data

(60) Provisional application No. 61/261,952, filed on Nov. 17, 2009.

(51) Int. Cl.
| | | |
|---|---|---|
| *C07H 21/04* | (2006.01) |
| *C12N 15/63* | (2006.01) |
| *C07K 5/00* | (2006.01) |
| *C07K 14/47* | (2006.01) |

(52) U.S. Cl.
CPC ..................................... *C07K 14/47* (2013.01)
USPC ........................ 536/23.1; 435/320.1; 530/300

(58) Field of Classification Search
CPC ............................ C12N 15/113; C12Q 1/6886
See application file for complete search history.

(56) References Cited

U.S. PATENT DOCUMENTS

| | | | |
|---|---|---|---|
| 2007/0083334 A1 | 4/2007 | Mintz et al. |
| 2008/0187512 A1 | 8/2008 | Li |

FOREIGN PATENT DOCUMENTS

| | | | | |
|---|---|---|---|---|
| WO | WO 2004/078130 A2 | * | 9/2004 | .................. 514/44 |
| WO | WO 2005/113812 A2 | * | 12/2005 | .................. 435/6 |
| WO | WO 2009/151546 | | 12/2009 | |
| WO | WO 2010/019236 | | 2/2010 | |

OTHER PUBLICATIONS

Burnett et al., "Regulation of SMN protein stability." 2009, Mol Cell Biol 29(5):1107-15.
Chang et al., "Degradation of survival motor neuron (SMN) protein is mediated via the ubiquitin/proteasome pathway." 2004, Neuroschem Int 45(7):1107-12.
Heier et al., "Translational readthrough by the aminoglycoside geneticin (G418) modulates SMN stability in vitro and improves motor function in SMA mice in vivo." 2009, Hum Mol Genet 18(7):1310-22.
Lorson et al., "A single nucleotide in the SMN gene regulates splicing and is responsible for spinal muscular atrophy." 1999 Proc Natl Acad Sci USA 96(11):6307-11.
Mattis et al., "A SMNDelta7 read-through product confers functionality to the SMNDelta7 protein." 2008, Neurosci Lett 442(1):54-8.
Pellizzoni et al., "SMN mutants of spinal muscular atrophy patients are defective in binding to snRNP proteins." 1999, Proc Natl Acad Sci USA 96(20):11167-72.
Talbot et al., "Missense mutation clustering in the survival motor neuron gene: a role for a conserved tyrosine and glycine rich region of the protein in RNA metabolism?" 1997 Hum Mol Genet 6(3):497-500.
Wan et al., "Inactivation of the SMN complex by oxidative stress." 2008, Mol Cell 31(2):244-54.
Wang and Dreyfuss., "A cell system with targeted disruption of the SMN gene: functional conservation of the SMN protein and dependence of Gemin2 on SMN." 2001, J Biol Chem 276(13):9599-605.
Zhang et al., "An in vivo reporter system for measuring increased inclusion of exon 7 in SMN2 mRNA: potential therapy of SMA." 2001, Gene Therapy 8(20):1532-1638.
Prior et al., "A positive modifier of spinal muscular atrophy in the SMN2 gene." 2009, Am J Hum Genet 85(3):408-413.
Workman et al., "A SMN missense mutation complements SMN2 restoring snRNPs and rescuing SMA mice." 2009, Hum Mol Genet 18(12):2215-2229.
Yuo et al., "5-(N-ethyl-N-isopropyl)-amiloride enhances SMN2 exon 7 inclusion and protein expression in spinal muscular atrophy cells." 2008, Ann Neurol 63(1):26-34.

* cited by examiner

*Primary Examiner* — Amy Bowman
(74) *Attorney, Agent, or Firm* — Riverside Law LLP

(57) ABSTRACT

The present invention includes an isolated nucleic acid comprising a nucleic acid sequence encoding a SMNΔ7 degron and the encoded polypeptide. The invention also includes inhibitors of SMNΔ7 degron. The invention also includes compositions and methods for mitigating SMN deficiency by targeting inhibition of factors that mediate SMNΔ7-degron dependent degradation of SMNΔ7.

2 Claims, 5 Drawing Sheets

SEQUENCE LISTING

```
<160> NUMBER OF SEQ ID NOS: 25

<210> SEQ ID NO 1
<211> LENGTH: 885
<212> TYPE: DNA
<213> ORGANISM: Homo sapiens

<400> SEQUENCE: 1
atggcgatga gcagcggcgg cagtggtggc ggcgtcccgg agcaggagga ttccgtgctg      60
ttccggcgcg gcacaggcca gagcgatgat tctgacatttt gggatgatac agcactgata     120
aaagcatatg ataaagctgt ggcttcattt aagcatgctc taaagaatgg tgacatttgt     180
gaaacttcgg gtaaaccaaa aaccacacct aaaagaaaac ctgctaagaa gaataaaagc     240
caaaagaaga atactgcagc ttccttacaa cagtggaaag ttggggacaa atgttctgcc     300
atttggtcag aagacggttg catttaccca gctaccattg cttcaattga ttttaagaga     360
gaaacctgtg ttgtggttta cactggatat ggaaatagag aggagcaaaa tctgtccgat     420
ctactttccc caatctgtga agtagctaat aatatagaac aaaatgctca agagaatgaa     480
aatgaaagct aagtttcaac agatgaaagt gagaactcca ggtctcctgg aaataaatca     540
gataacatca agcccaaatc tgctccatgg aactcttttc tccctccacc accccccatg     600
ccagggccaa gactgggacc aggaaagcca ggtctaaaat tcaatggccc accaccgcca     660
ccgccaccac caccacccca cttactatca tgctggctgc ctccatttcc ttctggacca     720
ccaataattc ccccaccacc tcccatatgt ccagattctc ttgatgatgc tgatgctttg     780
ggaagtatgt taatttcatg gtacatgagt ggctatcata ctggctatta tatgggtttc     840
agacaaaatc aaaaagaagg aaggtgctca cattccttaa attaa                      885

<210> SEQ ID NO 2
<211> LENGTH: 294
<212> TYPE: PRT
<213> ORGANISM: Homo sapiens
```

<400> SEQUENCE: 2

```
Met Ala Met Ser Ser Gly Gly Ser Gly Gly Gly Val Pro Glu Gln Glu
1               5                   10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Met Pro Gly Pro Arg Leu Gly Pro Gly
        195                 200                 205

Lys Pro Gly Leu Lys Phe Asn Gly Pro Pro Pro Pro Pro Pro Pro
210                 215                 220

Pro Pro His Leu Leu Ser Cys Trp Leu Pro Pro Phe Pro Ser Gly Pro
225                 230                 235                 240

Pro Ile Ile Pro Pro Pro Pro Ile Cys Pro Asp Ser Leu Asp Asp
            245                 250                 255

Ala Asp Ala Leu Gly Ser Met Leu Ile Ser Trp Tyr Met Ser Gly Tyr
            260                 265                 270

His Thr Gly Tyr Tyr Met Gly Phe Arg Gln Asn Gln Lys Glu Gly Arg
            275                 280                 285

Cys Ser His Ser Leu Asn
    290
```

<210> SEQ ID NO 3
<211> LENGTH: 849
<212> TYPE: DNA
<213> ORGANISM: Homo sapiens

<400> SEQUENCE: 3

```
atggcgatga gcagcggcgg cagtggtggc ggcgtcccgg agcaggagga ttccgtgctg    60
ttccggcgcg gcacaggcca gagcgatgat tctgacattt gggatgatac agcactgata   120
aaagcatatg ataaagctgt ggcttcattt aagcatgctc taaagaatgg tgacatttgt   180
gaaacttcgg gtaaaccaaa aaccacacct aaaagaaaac tgctaagaa gaataaaagc   240 caaaagaaga atactgcagc ttccttacaa cagtggaaag ttggggacaa atgttctgcc   300
atttggtcag aagacggttg catttaccca gctaccattg cttcaattga ttttaagaga   360
```

```
gaaacctgtg ttgtggttta cactggatat ggaaatagag aggagcaaaa tctgtccgat    420
ctactttccc caatctgtga agtagctaat aatatagaac aaaatgctca agagaatgaa    480
aatgaaagcc aagtttcaac agatgaaagt gagaactcca ggtctcctgg aaataaatca    540
gataacatca agcccaaatc tgctccatgg aactcttttc tccctccacc acccccatg     600 ccagggccaa gactgggacc aggaaagcca ggtctaaaat tcaatggccc accaccgcca    660
ccgccaccac caccaccca cttactatca tgctggctgc ctccattcc ttctggacca     720 ccaataattc ccccaccacc tcccatatgt ccagattctc ttgatgatgc tgatgctttg    780
ggaagtatgt taatttcatg gtacatgagt ggctatcata ctggctatta tatggaaatg    840
ctggcatag                                                            849
```

<210> SEQ ID NO 4
<211> LENGTH: 282
<212> TYPE: PRT
<213> ORGANISM: Homo sapiens

<400> SEQUENCE: 4

```
Met Ala Met Ser Ser Gly Gly Ser Gly Gly Gly Val Pro Glu Gln Glu
1               5                   10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Pro Met Pro Gly Pro Arg Leu Gly Pro Gly
        195                 200                 205

Lys Pro Gly Leu Lys Phe Asn Gly Pro Pro Pro Pro Pro Pro
    210                 215                 220

Pro Pro His Leu Leu Ser Cys Trp Leu Pro Pro Phe Pro Ser Gly Pro
225                 230                 235                 240

Pro Ile Ile Pro Pro Pro Pro Ile Cys Pro Asp Ser Leu Asp Asp
                245                 250                 255

Ala Asp Ala Leu Gly Ser Met Leu Ile Ser Trp Tyr Met Ser Gly Tyr
            260                 265                 270

His Thr Gly Tyr Tyr Met Glu Met Leu Ala
        275                 280
```

<210> SEQ ID NO 5
<211> LENGTH: 885
<212> TYPE: DNA
<213> ORGANISM: Homo sapiens

<400> SEQUENCE: 5

```
atggcgatga gcagcggcgg cagtggtggc ggcgtcccgg agcaggagga ttccgtgctg      60
ttccggcgcg gcacaggcca gagcgatgat tctgacattt gggatgatac agcactgata     120
aaagcatatg ataaagctgt ggcttcattt aagcatgctc taaagaatgg tgacatttgt     180
gaaacttcgg gtaaaccaaa accacacct aaaagaaaac ctgctaagaa gaataaaagc     240
caaaagaaga atactgcagc ttccttacaa cagtggaaag ttggggacaa atgttctgcc     300
atttggtcag aagacggttg catttaccca gctaccattg cttcaattga ttttaagaga     360
gaaacctgtg ttgtggttta cactggatat ggaaatagag aggagcaaaa tctgtccgat     420
ctactttccc caatctgtga agtagctaat aatatagaac aaaatgctca agagaatgaa     480
aatgaaagcc aagtttcaac agatgaaagt gagaactcca ggtctcctgg aaataaatca     540
gataacatca agcccaaatc tgctccatgg aactcttttc tccctccacc accccccatg     600
ccagggccaa gactgggacc aggaaagcca ggtctaaaat tcaatggccc accaccgcca     660
ccgccaccac caccacccca cttactatca tgctggctgc ctccatttcc ttctggacca     720
ccaataattc ccccaccacc tcccatatgt ccagattctc ttgatgatgc tgatgctttg     780
ggaagtatgt taatttcatg gtacatgagt ggctatcata ctggctatta tatgggtttt     840
agacaaaatc aaaaagaagg aaggtgctca cattccttaa attaa                    885
```

<210> SEQ ID NO 6
<211> LENGTH: 15
<212> TYPE: PRT
<213> ORGANISM: Artificial Sequence
<220> FEATURE:
<223> OTHER INFORMATION: Chemically synthesized

<400> SEQUENCE: 6

Tyr Met Ser Gly Tyr His Thr Gly Tyr Tyr Met Glu Met Leu Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Chemically synthesized

<400> SEQUENCE: 7

Ala Met Ser Gly Tyr His Thr Gly Tyr Tyr Met Glu Met Leu Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Chemically synthesized

<400> SEQUENCE: 8

Tyr Met Ala Gly Tyr His Thr Gly Tyr Tyr Met Glu Met Leu Ala
1               5                   10                  15

```
<210> SEQ ID NO 9
<211> LENGTH: 15
<212> TYPE: PRT
<213> ORGANISM: Artificial Sequence
<220> FEATURE:
<223> OTHER INFORMATION: Chemically synthesized

<400> SEQUENCE: 9

Tyr Met Ser Gly Ala His Thr Gly Tyr Tyr Met Glu Met Leu Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Chemically synthesized

<400> SEQUENCE: 10

Tyr Met Ser Gly Tyr His Thr Gly Ala Tyr Met Glu Met Leu Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Chemically synthesized

<400> SEQUENCE: 11

Tyr Met Ser Gly Tyr His Thr Gly Ala Tyr Met Glu Met Leu Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Chemically synthesized

<400> SEQUENCE: 12

Tyr Met Ser Gly Tyr His Thr Gly Tyr Ala Met Glu Met Leu Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Chemically synthesized

<400> SEQUENCE: 13

Tyr Met Ser Gly Tyr His Thr Gly Tyr Tyr Ala Glu Met Leu Ala
1               5                   10                  15

<210> SEQ ID NO 14
<211> LENGTH: 48
<212> TYPE: DNA
<213> ORGANISM: Artificial Sequence
<220> FEATURE:
<223> OTHER INFORMATION: Chemically synthesized

<400> SEQUENCE: 14
tacatgagtg gctatcatac tggctattat atggaaatgc tggcatag         48

<210> SEQ ID NO 15
<211> LENGTH: 5
```

```
<212> TYPE: PRT
<213> ORGANISM: Artificial Sequence
<220> FEATURE:
<223> OTHER INFORMATION: Chemically synthesized

<400> SEQUENCE: 15

Asp Asp Asp Asp Lys
1               5

<210> SEQ ID NO 16
<211> LENGTH: 4
<212> TYPE: PRT
<213> ORGANISM: Artificial Sequence
<220> FEATURE:
<223> OTHER INFORMATION: Chemically synthesized

<400> SEQUENCE: 16

Ile Glu Gly Arg
1

<210> SEQ ID NO 17
<211> LENGTH: 4
<212> TYPE: PRT
<213> ORGANISM: Artificial Sequence
<220> FEATURE:
<223> OTHER INFORMATION: Chemically synthesized

<400> SEQUENCE: 17

Ile Asp Gly Arg
1

<210> SEQ ID NO 18
<211> LENGTH: 6
<212> TYPE: PRT
<213> ORGANISM: Artificial Sequence
<220> FEATURE:
<223> OTHER INFORMATION: Chemically synthesized

<400> SEQUENCE: 18

Leu Val Pro Arg Gly Ser
1               5

<210> SEQ ID NO 19
<211> LENGTH: 7
<212> TYPE: PRT
<213> ORGANISM: Artificial Sequence
<220> FEATURE:
<223> OTHER INFORMATION: Chemically synthesized

<400> SEQUENCE: 19

Glu Asn Leu Tyr Phe Gln Gly
1               5

<210> SEQ ID NO 20
<211> LENGTH: 8
<212> TYPE: PRT
<213> ORGANISM: Artificial Sequence
<220> FEATURE:
<223> OTHER INFORMATION: Chemically synthesized

<400> SEQUENCE: 20

Leu Glu Val Leu Phe Gln Gly Pro
1               5

<210> SEQ ID NO 21
<211> LENGTH: 12
<212> TYPE: PRT
```

```
<213> ORGANISM: Artificial Sequence
<220> FEATURE:
<223> OTHER INFORMATION: Chemically synthesized

<400> SEQUENCE: 21

Cys Met His Ile Glu Ser Leu Asp Ser Tyr Thr Cys
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Chemically synthesized

<400> SEQUENCE: 22

Cys Met Thr Ile Glu Ala Leu Asp Lys Tyr Ala Cys
1               5                   10

<210> SEQ ID NO 23
<211> LENGTH: 32
<212> TYPE: PRT
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (1)..(3)
<223> OTHER INFORMATION: Xaa can be any naturally occurring amino acid

<400> SEQUENCE: 23

Xaa Xaa Xaa Glu Ala Ala Leu Ala Glu Ala Leu Ala Glu Ala Leu Ala
1               5                   10                  15

Glu Ala Leu Ala Glu Ala Leu Ala Glu Ala Leu Glu Ala Leu Ala Ala
            20                  25                  30

<210> SEQ ID NO 24
<211> LENGTH: 8
<212> TYPE: PRT
<213> ORGANISM: Artificial Sequence
<220> FEATURE:
<223> OTHER INFORMATION: Chemically synthesized

<400> SEQUENCE: 24

Gly Asn Ala Ala Ala Ala Arg Arg
1               5

<210> SEQ ID NO 25
<211> LENGTH: 10
<212> TYPE: PRT
<213> ORGANISM: Artificial Sequence
<220> FEATURE:
<223> OTHER INFORMATION: Chemically synthesized

<400> SEQUENCE: 25

Cys Asp Pro Gly Tyr Ile Gly Ser Arg Cys
1               5                   10
```

SMNDELTA7 DEGRON: NOVEL COMPOSITIONS AND METHODS OF USE

CROSS-REFERENCE TO RELATED APPLICATION

This application is the U.S. national phase application filed under 35 U.S.C. §371 claiming benefit to International Patent Application No. PCT/US2010/056985, filed on Nov. 17, 2010, which is entitled to priority under 35 U.S.C. §119(e) to U.S. Provisional Patent Application No. 61/261,952, filed on Nov. 17, 2009, each of which application is hereby incorporated herein by reference in its entirety.

BACKGROUND OF THE INVENTION

Spinal muscular atrophy (SMA) is a common and often fatal, motor neuron degenerative disease and a leading genetic cause of infant mortality (Talbot et al., 2001, Semin Neurol 21(2):189-97; Wirth et al., 2006, Semin Pediatr Neurol 13(2):121-31). SMA severity corresponds to the degree of functional survival of motor neurons (SMN) protein deficiency. SMN is a ubiquitously expressed protein that plays a critical role in RNA metabolism and is essential for viability of all cells in eukaryotes (Neuenkirchen et al., 2008, FEBS Lett 582(14):1997-2003; Yong, et al., 2004, Trends Cell Biol 14(5):226-32). As part of a large multi-protein complex, the SMN complex, SMN functions in the biogenesis of snRNPs, the major subunits of the spliceosome (Meister et al., 2001, Nat Cell Biol 3(11):945-9; Pellizzoni et al., 2002, Science 298(5599):1775-9; Liu et al., 1997, Cell 90(6):1013-21; Fischer et al., 1997, Cell 90(6):1023-9).

Although SMN deficiency manifests itself as a motor neuron disease, its molecular consequences are evident as profound disruptions in RNA metabolism in all tissues tested in a SMA mouse model (Zhang et al., 2008, Cell 133(4):585-600). There are two SMN genes in humans, SMN1 and SMN2, both encoding the same open reading frame. The vast majority of SMA patients have homozygous SMN1 deletions and are sustained by one or more copies of SMN2. However, due to a C/T substitution at position 6 of exon 7 that does not change the encoded amino acid, the splicing of the SMN2 pre-mRNA incurs frequent (~80%) exon 7 skipping. This produces an SMN protein (SMNΔ7) that lacks the normal carboxyl-terminal 16 amino acids, and acquires instead four amino acids, EMLA, encoded by exon 8 (Le et al., 2005, Hum Mol Genet 14(6):845-57). Thus, BIM deletions expose the splicing defect of SMN2 and its ineffectiveness in producing full-length normal SMN protein (Wirth et al., 2006, Semin Pediatr Neurol 13(2):121-31; Cooper et al., 2009, Cell 136(4):777-93).

Biochemical experiments in vitro suggest that SMNΔ7 is not fully functional compared to normal SMN protein, including a diminished oligomerization and binding to protein substrates, such as the snRNP Sm proteins (Pellizzoni et al., 1999, Proc Natl Acad Sci USA 96(20):11167-72; Lorson et al., 1998, Nat Genet 19(1):63-6).

Increased SMN2 copy number correlates with a milder clinical phenotype in SMA patients (Wirth et al., 2006, Hum Genet 119(4):422-8). Furthermore, studies in cells suggest (Wang et al., 2001, J Biol Chem 276(48):45387-93) and experiments in SMN-deficient mice demonstrate that expression of an increasing copy number of SMNΔ7 cDNA transgenes proportionately lessens SMA severity (Le et al., 2005, Hum Mol Genet 14(6):845-57). This suggests that even a modest SMNΔ7 increase is beneficial in SMA.

There is a long-standing need to identify the cause of SMNΔ7 instability in order to correct the deficit in vivo. The present invention fills this need.

SUMMARY OF THE INVENTION

The present invention includes an isolated nucleic acid comprising a nucleic acid sequence encoding a SMNΔ7 degron. Preferably, the nucleic acid sequence is SEQ ID NO. 3 or SEQ ID NO. 14.

In one embodiment, the invention comprises a promoter operably linked to the nucleic acid sequence of SEQ ID NO. 3 or SEQ ID NO. 14.

In one embodiment, the promoter is a regulated promoter.
In one embodiment, the promoter is an inducible promoter.
In one embodiment, the promoter is a repressible promoter.

The invention also includes an isolated polypeptide comprising a SMNΔ7 degron. Preferably, the polypeptide is selected from the group consisting of SEQ ID NO. 6, SEQ ID NO. 7, SEQ ID NO. 9, SEQ ID NO. 10. SEQ ID NO. 11, SEQ ID NO. 12, and SEQ ID NO. 13.

In one embodiment, the isolated polypeptide prevents degradation of a protein. Preferably, the isolated polypeptide comprises SEQ ID NO. 8.

The invention also includes an isolated nucleic acid comprising a nucleic acid sequence encoding a fusion polypeptide comprising a reporter protein and a protein destabilization sequence. Preferably, the fusion polypeptide has a reduced half-life relative to a corresponding reporter protein which lacks the protein destabilization sequence.

In one embodiment, the protein destabilization sequence comprises SEQ ID NO. 6.

The invention includes an isolated nucleic acid comprising a nucleic acid sequence encoding a fusion polypeptide comprising a reporter protein and at a protein stabilization sequence, which fusion polypeptide has an increased half-life relative to a corresponding reporter protein which lacks said protein stabilization sequence.

In one embodiment, the protein stabilization sequence comprises SEQ ID NO. 8.

The invention includes a pharmaceutical composition comprising an inhibitor of SMNΔ7 degron. Preferably, the inhibitor stabilizes SMNΔ7 protein in a cell.

In one embodiment, the inhibitor is selected from the group consisting of an siRNA, a ribozyme, an antisense, an aptamer, a peptidomimetic, a small molecule, and any combination thereof.

The invention includes a method of preventing the degradation of SMNΔ7 protein in a cell. The method comprises contacting the SMNΔ7 protein with an effective amount of a SMNΔ7 degron inhibitor, wherein when the SMNΔ7 degron is contacted with the inhibitor, the activity of the SMNΔ7 degron is inhibited and the SMNΔ7 protein is not degraded.

In one embodiment, the cell is a mammalian cell. Preferably the mammalian cell is a human cell.

The invention includes a method of treating a mammal having spinal muscular atrophy (SMA). The method comprises administering to the mammal in need thereof an effective amount of a SMNΔ7 degron inhibitor, wherein when the inhibitor inhibits the activity of said SMNΔ7 degron, the degradation of SMNΔ7 protein is prevented, thereby treating SMA.

In one embodiment, the mammal is a human.

The invention includes a vector encoding an isolated polypeptide selected from the group consisting of SEQ ID NO. 4, SEQ ID NO. 6, SEQ ID NO. 7, SEQ ID NO. 8, SEQ ID NO. 9, SEQ ID NO. 10, SEQ ID NO. 11, SEQ ID NO. 12, and SEQ ID NO. 13.

The invention includes a recombinant cell comprising a vector encoding an isolated polypeptide selected from the group consisting of SEQ ID NO. 4, SEQ ID NO. 6, SEQ ID NO. 7, SEQ ID NO. 8, SEQ ID NO. 9, SEQ ID NO. 10, SEQ ID NO. 11, SEQ ID NO. 12, and SEQ NO. 13.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A and FIG. 1B, is a series of images depicting delineation of YG+EMLA as a protein destabilization sequence in SMNΔ7. FIG. 1A depicts a schematic diagram of luciferase (Luc)-fused SMN and a series of deletion constructs used for quantitative measurement of protein stability. YG box denotes the tyrosine/glycine (YG)-rich sequences in exon 6 of SMN. The EMLA sequence encoded by exon 8 is depicted by the box at the C-terminal end of SMNΔ7.

FIG. 1B is a graph of luciferase activity in cells transected with the indicated constructs following treatment with CHX (0.1 mg/ml). Luciferase activity at each time point was calculated by comparison to those at time 0, which was set to 100%. 50% activity is indicated by the gray dotted line. Error bars represent standard deviation (SD) from three independent experiments.

FIG. 2A and FIG. 2B, is a series of images depicting the effect of the carboxyl terminus of SMNΔ7, YG+EMLA, as a strong protein destabilizing signal (degron). FIG. 2A depicts a gel from a Western blot using an anti-GFP antibody to determine the effect of CHX treatment for the indicated times on GFP-YG+EMLA or -NS (nonspecific sequence) protein stability. Magoh was used as a loading control. FIG. 2B is a graph depicting luciferase activity as a function of CHX treatment for various proteins including a comparison of YG+EMLA and Exon6+EMLA of SMNΔ7 with an optimized protein destabilizing element (optiPEST). Shown also are Luc-SMN and LucSMNΔ7 containing additional five amino acids at the C-terminal end (SMNΔ7+5aa). Error bars represent SDs from three independent experiments.

FIG. 3A through FIG. 3D, is a series of images depicting the importance of residue S270 for the activity of the SMNΔ7-DEG through YG+EMLA. FIG. 3A is a schematic illustration depicting seven residues in the YG box that were each mutated to alanine, as indicated. FIG. 2B depicts the results of Western blot analyses using an anti-HA tag antibody directed against HA-tagged SMN, SMNΔ7, and SMNΔ7$^{S270A}$ expressed in 293T cells treated with DMSO or 10 µM MG132 (MG) for 16 hours. Fusion proteins were monitored by, and Magoh was used as a control. FIG. 3C is a graph depicting the quantification of HA-tagged proteins depicted in FIG. 3B and compared to HA-SMN without MG132 treatment. Protein amount (%) for SMNΔ7, and SMNΔ7$^{S270A}$ are calculated relative to HA-SMN not treated with MG132, that is arbitrarily set to 100%. The fold change of each fusion protein amount upon MG132 treatment is indicated in red above the column. FIG. 3D depicts schematic illustrations of SMN, YG+EMLA, and YG+EMLA$^{S270A}$ constructs (top). All constructs had Luc fusions. Luciferase activity as a function of CHX treatment is depicted below. Error bars represent SDs from three independent experiments.

FIG. 4A through FIG. 4D, is a series of images depicting the functionality of SMNΔ7$^{S270A}$ in snRNP assembly and its ability to rescue SMN-deficient cells. FIG. 4 A is a series of panels depicting S5 cells cultured in the presence of tetracycline (1 µg/ml) to deplete endogenous SMN and infected with retroviruses expressing SMN, SMNΔ7, or SMNΔ7$^{S270A}$. FIG. 4B is a graph depicting cell growth as in FIG. 4A measured by monitoring the number of live cells at the indicated time points following tetracycline addition. FIG. 4C depicts the results of Western blot analyses of SMN protein in rescued cells (10 days after tetracycline addition). FIG. 4D is a graph depicting SMN complex activity (%) as measured by in vitro snRNP assembly on U4 snRNA in cytoplasmic extracts from rescued cells, using U4ΔSm RNA as a control.

DETAILED DESCRIPTION OF THE INVENTION

Figure 1:
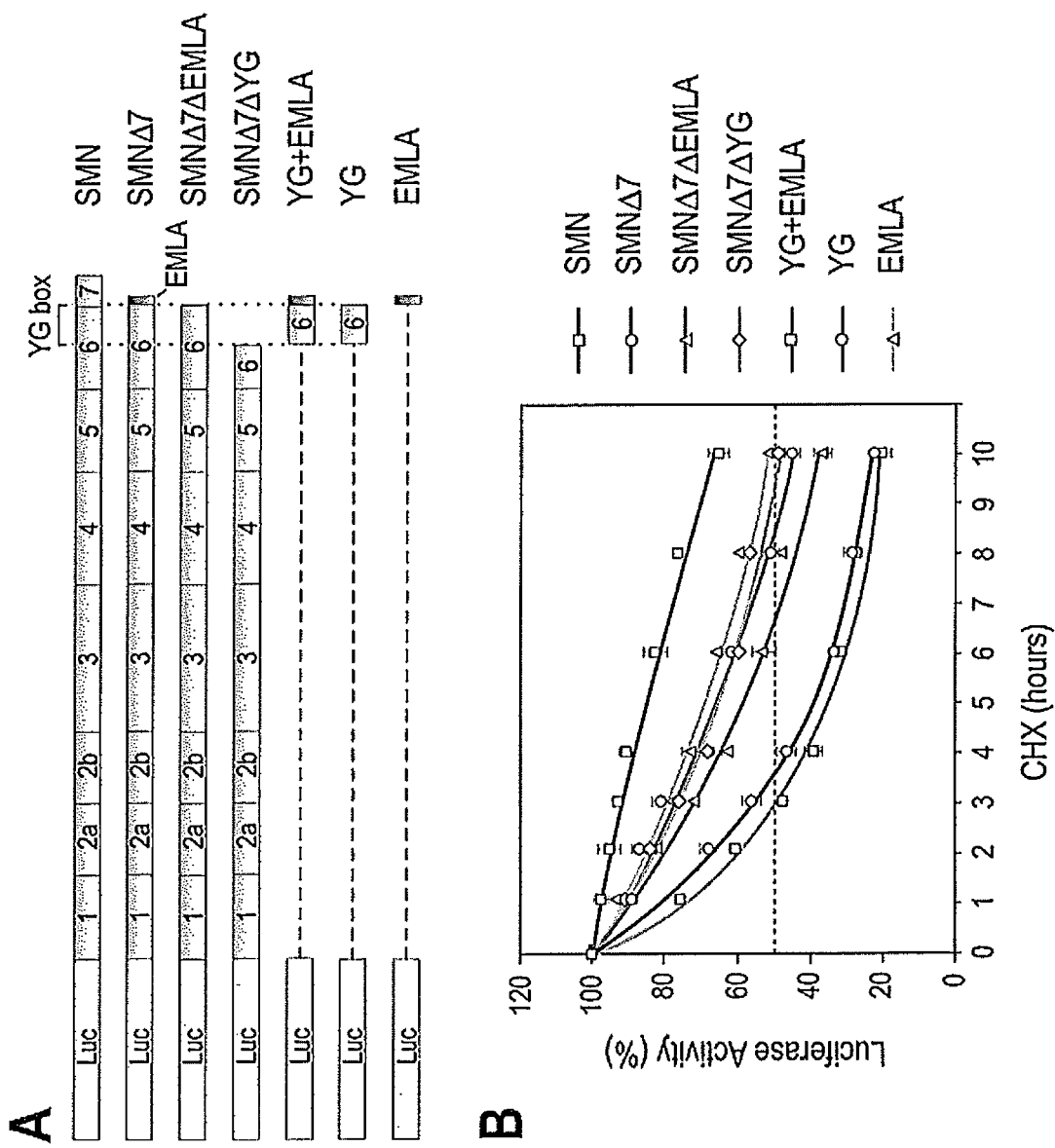
FIG. 1, comprising

The present invention is based on the discovery of a novel protein destabilization signal present on the C-terminus of SMNΔ7 (SEQ ID NO. 4), referred to herein as SMNΔ7-degron (SEQ ID NO. 6). SMNΔ7-degron is sufficient to induce protein instability and degradation of heterologously expressed proteins. The instability of SMN due to the presence of the 15 amino acid peptide SMNΔ7-degron results in SMN deficiency in a cell. An SMN protein deficiency impairs mRNA metabolism in a cell and contributes to the severity of the clinical phenotype observed in SMA patients.

In another embodiment, the 15 amino acid peptide SMNΔ7-degron (SEQ ID NO. 6) induces instability and degradation of a heterologously expressed protein in a cell. The heterologously expressed protein of interest may comprise the SMNΔ7-degron at its C-terminus.

In another embodiment the present invention includes a point mutation in the SMNΔ7-degron, SMNΔ7$^{S270A}$ (SEQ ID NO. 8), that enhances protein stability. In one aspect, SMNΔ7$^{s27n}$ (SEQ ID NO. 8) prevents SMN degradation and subsequent depletion, thereby increasing the viability of SMN-depleted cells.

Accordingly, in yet another embodiment, the present invention includes compositions and methods for mitigating SMN deficiency by targeting inhibition of factors that mediate SMNΔ7-degron dependent degradation of SMNΔ7. In still another embodiment, the present invention provides compositions and methods for mitigating deleterious effects of protein instability or degradation in a cell.

In another embodiment, the present invention includes a method of identifying therapeutic agents that are SMNΔ7-degron inhibitors.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator," as the term is used herein, is meant any device including, but not limited to, a hypodermic syringe, a pipette, and the like, for administering the compounds and compositions of the invention.

As used herein, "aptamer" refers to a small molecule that can bind specifically to another molecule. Aptamers are typically either polynucleotide- or peptide-based molecules. A polynucleotidal aptamer is a DNA or RNA molecule, usually comprising several strands of nucleic acids, that adopt highly specific three-dimensional conformation designed to have appropriate binding affinities and specificities towards specific target molecules, such as peptides, proteins, drugs, vitamins, among other organic and inorganic molecules. Such polynucleotidal aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T and G:C nucleotide pairs).

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

Signal transduction is any process by which a cell converts one signal or stimulus into another, most often involving ordered sequences of biochemical reactions carried out within the cell. The number of proteins and molecules participating in these events increases as the process eminates from the initial stimulus resulting in a "signal cascade." The phrase "downstream effector", as used herein, refers to a protein or molecule acted upon during a signaling cascade, which in term acts upon another protein or molecule. The term "downstream" indicates the direction of the signaling cascade.

A disease or disorder is "alleviated" if the severity of a symptom of the disease, or disorder, the frequency with which such a symptom is experienced by a patient, or both, are reduced.

The terms "effective amount" and "pharmaceutically effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "fusion polypeptide" refers to a chimeric protein containing a protein of interest (e.g., luciferase) joined to a heterologous sequence (e.g., a non-luciferase amino acid or protein).

The term "homology" refers to a degree of complementarity. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonueleotide may be present in single-stranded or double-stranded form. When an isolated nucleic acid or oligonucleotide is to be utilized to express a protein, the oligonucleotide contains at a minimum, the sense or coding strand (i.e., the oligonucleotide may be single-stranded), but may contain both the sense and anti-sense strands (i.e., the oligonucleotide may be double-stranded).

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By "expression cassette" is meant a nucleic acid molecule comprising a coding sequence operably linked to promoter/regulatory sequences necessary for transcription and, optionally, translation of the coding sequence.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a n inducible manner.

An "inducible" promoter is a nucleotide sequence which, when operably linked with a polynucleotide which encodes or specifies a gene product, causes the gene product to be produced substantially only when an inducer which corresponds to the promoter is present.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, a "peptidomimetic" is a compound containing non-peptidic structural elements that is capable of mimicking the biological action of a parent peptide. A peptidomimetic may or may not comprise peptide bonds.

A "polynucleotide" means a single strand or parallel and anti-parallel strands of a nucleic acid. Thus, a polynucleotide may be either a single-stranded or a double-stranded nucleic acid. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

The term "recombinant polypeptide" as used herein is defined as a polypeptide produced by using recombinant DNA methods. A host cell that comprises a recombinant polynucleotide is referred to as a "recombinant host cell." A gene which is expressed in a recombinant host cell wherein the gene comprises a recombinant polynucleotide, produces a "recombinant polypeptide."

As used herein, a "recombinant cell" is a host cell that comprises a recombinant polynucleotide.

"Ribozymes" as used herein are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med, Assn. 260:3030). There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules. Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053).

By the term "specifically binds," as used herein, is meant a molecule, such as an antibody, which recognizes and binds to another molecule or feature, but does not substantially recognize or bind other molecules or features in a sample.

As used herein, the term "transdominant negative mutant gene" refers to a gene encoding a polypeptide or protein product that prevents other copies of the same gene or gene product, which have not been mutated (i.e., which have the wild-type sequence) from functioning properly (e.g., by inhibiting wild type protein function). The product of a transdominant negative mutant gene is referred to herein as "dominant negative" or "DN" (e.g., a dominant negative protein, or a DN protein).

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

The phrase "SMNΔ7 degron inhibitor," as used herein, refers to a composition or compound that inhibits SMNΔ7 degron activity, either directly or indirectly, using any method known to the skilled artisan. A SMNΔ7 degron inhibitor may be any type of compound, including but not limited to, a polypeptide, a nucleic acid, an aptamer, a peptidometic, and a small molecule.

As used herein, a "marker gene" or "reporter gene" is a gene that imparts a distinct phenotype to cells expressing the gene and thus permits cells having the gene to be distinguished from cells that do not have the gene. Such genes may encode either a selectable or screenable marker, depending on whether the marker confers a trait which one can 'select' for by chemical means, i.e., through the use of a selective agent (e.g., a herbicide, antibiotic, or the like), or whether it is simply a "reporter" trait that one can identify through observation or testing, i.e., by 'screening'. Elements of the present disclosure are exemplified in detail through the use of particular marker genes. Of course, many examples of suitable marker genes or reporter genes are known to the art and can be employed in the practice of the invention. Therefore, it will be understood that the following discussion is exemplary rather than exhaustive. In light of the techniques disclosed herein and the general recombinant techniques which are known in the art, the present invention renders possible the alteration of any gene.

Exemplary genes include, but are not limited to, a neo gene, a β-gal gene, a gus gene, a cat gene, a gpt gene, a hyg gene, a hisD gene, a ble gene, a mprt gene, a bar gene, a nitrilase gene, a mutant acetolactate synthase gene (ALS) or acetoacid synthase gene (AAS), a methotrexate-resistant dhfr gene, a dalapon dehalogenase gene, a mutated anthranilate synthase gene that confers resistance to 5-methyl tryptophan (WO 97/26366), an R-locus gene, a β-lactamase gene, a xy/E gene, an α-amylase gene, a tyrosinase gene, a luciferase (luc) gene, (e.g., a *Renilla reniformis* luciferase gene, a firefly luciferase gene, or a click beetle luciferase (*Pyrophorus plagiophthalamus*) gene, an aequorin gene, or a green fluorescent protein gene. Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA, and proteins that are inserted or trapped in the cell membrane.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

It is understood that any and all whole or partial integers between any ranges set forth herein are included herein.

DESCRIPTION

1. Compositions
A. Polypeptides

The invention includes a polypeptide comprising a novel protein destabilizing signal, SMNΔ7-degron (SEQ ID NO. 6). Other polypeptides of the invention derived from SMNΔ7-degron (SEQ ID NO. 6) which act to destabilize a protein include SEQ ID NO. 7, SEQ ID NO. 9, SEQ ID NO. 10, SEQ ID NO. 11, SEQ ID NO. 12, and SEQ ID NO. 13. As used herein, a "protein destabilization signal" is a polypeptide sequence expressed on either the N- or C-terminus of a protein which shortens the half life of that protein relative to the same protein that does not express the protein destabilization signal.

In another embodiment, the invention includes a polypeptide comprising a protein stabilization signal, SMNΔ7$^{S270A}$ (SEQ ID NO. 8) that prevents or reduces protein degradation.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two polypeptides is determined by comparing the amino acid sequence and its conserved amino acid substitutes of one polypeptide to a sequence of a second polypeptide. Variants are defined to include polypeptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to ubiquitin or to a ubiquitylated protein. The present invention includes amino acid sequences that are at least 60%, 65%, 70%, 72%, 74%, 76%, 78%, 80%, 90%, or 95% similar or identical to the original amino acid sequence. The degree of identity between two polypeptides is determined using computer algorithms and methods that are widely known for the persons skilled in the art. The identity between two amino acid sequences is preferably determined by using the BLASTP algorithm [BLAST Manual, Altschul, S., et al., NCB1 NLM NIH Bethesda, Md. 20894, Altschul, S., et al., J. Mol. Biol. 215: 403-410 (1990)].

The polypeptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine mierosomal membranes or *Xenopus* egg extracts (U.S. Pat. No. 6,103,489) to a standard translation reaction.

The polypeptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA (tRNA$_{LYS}$), could be modified with an amine specific photoaffinity label.

The term "functionally equivalent" as used herein refers to a polypeptide according to the invention that preferably retains at least one biological function or activity of the specific amino acid sequence of either a SMNΔ7-degron or SMNΔ7$^{S270A}$.

1. Fusion and Chimeric Polypeptides

A SMNΔ7-degron or SMNΔ7$^{S270A}$, or chimeric protein of the invention may be conjugated with other molecules, such as proteins, to prepare fusion proteins. This may be accomplished, for example, by the synthesis of N-terminal or C-terminal fusion proteins provided that the resulting fusion protein retains the functionality of the SMNΔ7-degron or SMNΔ7$^{S270A}$ protein.

A SMNΔ7-degron or SMNΔ7$^{s270A}$, or chimeric protein of the invention may be phosphorylated using conventional methods such as the method described in Reedijk et al. (The EMBO Journal 11(4):1365, 1992).

Cyclic derivatives of the peptides or chimeric proteins of the invention are also part of the present invention. Cyclization may allow the peptide or chimeric protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

(a) Tags

In a particular embodiment of the invention, the polypeptide of the invention further comprises the amino acid sequence of a tag. The tag includes but is not limited to: polyhistidine tags (His-tags) (for example H6 and H10, etc.) or other tags for use in IMAC systems, for example, $Ni^{2+}$ affinity columns, etc., GST fusions, MBP fusions, streptavidine-tags, the BSP biotinylation target sequence of the bacterial enzyme BMA and tag epitopes that are directed by antibodies (for example c-myc tags, FLAG-tags, among others). As will be observed by a person skilled in the art, the tag peptide can be used for purification, inspection, selection and/or visualization of the fusion protein of the invention. In a particular embodiment of the invention, the tag is a detection tag and/or a purification tag. It will be appreciated that the tag sequence will not interfere in the function of the protein of the invention.

(b) Leader and Secretory Sequences

Accordingly, the polypeptides of the invention can be fused to another polypeptide or tag, such as a leader or secretory sequence or a sequence which is employed for purification or for detection. In a particular embodiment, the polypeptide of the invention comprises the glutathione-S-transferase protein tag which provides the basis for rapid high-affinity purification of the polypeptide of the invention. Indeed, this GST-fusion protein can then be purified from cells via its high affinity for glutathione. Agarose beads can be coupled to glutathione, and such glutathione-agarose beads bind GST-proteins. Thus, in a particular embodiment of the invention, the polypeptide of the invention is bound to a solid support. In a preferred embodiment, if the polypeptide of the invention comprises a GST moiety, the polypeptide is coupled to a glutathione-modified support. In a particular case, the glutathione modified support is a glutathione-agarose bead. Additionally, a sequence encoding a protease cleavage site can be included between the affinity tag and the polypeptide sequence, thus permitting the removal of the binding tag after incubation with this specific enzyme and thus facilitating the purification of the corresponding protein of interest. Suitable protease cleavage sites for incorporation into the polypeptides of the invention include enterokinase (cleavage site Asp-Asp-Asp-Asp-Lys) (SEQ ID NO: 15), factor Xa (cleavage site Ile-Glu-Gly-Arg (SEQ ID NO:16) or Ile-Asp-Gly-Arg (SEQ ID NO: 17)), thrombin (cleavage site Leu-Vat-Pro-Arg-Gly-Ser) (SEQ ID NO: 18), TEV protease (cleavage site Glu-Asn-Leu-Tyr-Phe-Gln-Gly) (SEQ ID NO: 19), PreScission protease (cleavage site Leu-Glu-Val-Leu-Phe-Gln-Gly-Pro) (SEQ ID NO: 20), inteins and the like.

(c) Targeting Sequences

The invention also relates to novel chimeric proteins comprising at least one SMNΔ7-degron or SMNΔ7$^{S270A}$ peptide of the invention fused to, or integrated into, a target protein, and/or a targeting domain capable of directing the chimeric protein to a desired cellular component or cell type or tissue. The chimeric proteins may also contain additional amino acid sequences or domains. The chimeric proteins are recombinant in the sense that the various components are from different sources, and as such are not found together in nature (i.e. are heterologous).

A target protein is a protein that is selected for degradation and for example may be a protein that is mutated or over expressed in a disease or condition. In another embodiment of the invention, a target protein is a protein that is abnormally degraded and for example may be a protein that is mutated of underexpressed in a disease or condition. The targeting domain can be a membrane spanning domain, a membrane binding domain, or a sequence directing the protein to associate with for example vesicles or with the nucleus. The targeting domain can target a SMNΔ7-degron or SMNΔ7$^{S270A}$ peptide to a particular cell type or tissue. For example, the targeting domain can be a cell surface ligand or an antibody against cell surface antigens of a target tissue (e.g. neuron or tumor antigens). A targeting domain may target a SMNΔ7-degron or SMNΔ7$^{S270A}$ peptide to a cellular component.

(d) Intracellular Targeting

Combined with certain formulations, such peptides can be effective intracellular agents. However, in order to increase the efficacy of such peptides, the SMNΔ7-degron or SMNΔ7$^{S270A}$ peptide can be provided a fusion peptide along with a second peptide which promotes "transcytosis", e.g., uptake of the peptide by epithelial cells. To illustrate, the SMNΔ7-degron or SMNΔ7$^{S270A}$ peptide of the present invention can be provided as part of a fusion polypeptide with all or a fragment of the N-terminal domain of the HIV protein Tat, e.g., residues 1-72 of Tat or a smaller fragment thereof which can promote transcytosis. In other embodiments, the SMNΔ7-degron or SMNΔ7$^{S270A}$ peptide can be provided a fusion polypeptide with all or a portion of the antenopedia III protein.

To further illustrate, the SMNΔ7-degron or SMNΔ7$^{S270A}$ peptide (or peptidomimetic) can be provided as a chimeric peptide which includes a heterologous peptide sequence ("internalizing peptide") which drives the translocation of an extracellular form of a SMNΔ7-degron or SMNΔ7$^{S270A}$ peptide sequence across a cell membrane in order to facilitate intracellular localization of the SMNΔ7-degron or SMNΔ7$^{S270A}$ peptide. In this regard, the therapeutic SMNΔ7-degron or SMNΔ7$^{S270A}$ binding sequence is one which is active intracellularly. The internalizing peptide, by itself, is capable of crossing a cellular membrane by, e.g., transcytosis, at a relatively high rate. The internalizing peptide is conjugated, e.g., as a fusion protein, to the SMNΔ7-degron or SMNΔ7$^{S270A}$ peptide. The resulting chimeric peptide is transported into cells at a higher rate relative to the activator polypeptide alone to thereby provide an means for enhancing its introduction into cells to which it is applied.

In one embodiment, the internalizing peptide is derived from the *Drosophila antennapedia* protein, or homologs thereof. The 60 amino acid long homeodomain of the homeoprotein antennapedia has been demonstrated to translocate through biological membranes and can facilitate the translocation of heterologous polypeptides to which it is couples. See for example Derossi et al. (1994) J Biol Chem 269: 10444-10450; and Perez et al. (1992) J Cell Sci 102:717-722. Recently, it has been demonstrated that fragments as small as 16 amino acids long of this protein are sufficient to drive internalization. See Derossi et al. (1996) J Biol Chem 271: 18188-18193.

The present invention contemplates a SMNΔ7-degron or SMNΔ7$^{S270A}$ peptide or peptidomimetic sequence as described herein, and at least a portion of the Antennapedia protein (or homolog thereof) sufficient to increase the transmembrane transport of the chimeric protein, relative to the SMNΔ7-degron or SMNΔ7$^{S270A}$ peptide or peptidomimetic, by a statistically significant amount.

Another example of an internalizing peptide is the HIV transactivator (TAT) protein. This protein appears to be divided into four domains (Kuppuswamy et al. (1989) Nucl. Acids Res. 17:3551-3561). Purified TAT protein is taken up by cells in tissue culture (Frankel and Pabo, (1989) Cell, 55:1189-1193), and peptides, such as the fragment corresponding to residues 37-62 of TAT, are rapidly taken up by cell in vitro (Green and Loewenstein, (1989) Cell 55:1179-1188). The highly basic region mediates internalization and targeting of the internalizing moiety to the nucleus (Ruben et al., (1989) J. Virol. 63:1-8).

Another exemplary transcellular polypeptide can be generated to include a sufficient portion of mastoparan (T. Higashijima et al., (1990) J. Biol. Chem. 265:14176) to increase the transmembrane transport of the chimeric protein.

While not wishing to be bound by any particular theory, it is noted that hydrophilic polypeptides may be also be physiologically transported across the membrane barriers by coupling or conjugating the polypeptide to a transportable peptide which is capable of crossing the membrane by receptor-mediated transcytosis. Suitable internalizing peptides of this type can be generated using all or a portion of, e.g., a histone, insulin, transferrin, basic albumin, prolactin and insulin-like growth factor I (IGF-I), insulin-like growth factor II (IGF-II) or other growth factors. For instance, it has been found that an insulin fragment, showing affinity for the insulin receptor on capillary cells, and being less effective than insulin in blood sugar reduction, is capable of transmembrane transport by receptor-mediated transcytosis and can therefore serve as an internalizing peptide for the subject transcellular peptides and peptidomimetics. Preferred growth factor-derived internalizing peptides include EGF (epidermal growth factor)-derived peptides, such as CMHIESLDSYTC (SEQ ID NO. 21) and CMYIEALDKYAC (SEQ ID NO. 22); TGF-beta (transforming growth factor beta)-derived peptides; peptides derived from PDGF (platelet-derived growth factor) or PDGF-2; peptides derived from IGF-I (insulin-like growth factor) or IGF-II; and FGF (fibroblast growth factor)-derived peptides.

Another class of translocating/internalizing peptides exhibits pH-dependent membrane binding. For an internalizing peptide that assumes a helical conformation at an acidic pH, the internalizing peptide acquires the property of amphiphilicity, e.g., it has both hydrophobic and hydrophilic interfaces. More specifically, within a pH range of approximately 5.0-5.5, an internalizing peptide forms an alpha-helical, amphiphilic structure that facilitates insertion of the moiety into a target membrane. An alpha-helix-inducing acidic pH environment may be found, for example, in the low pH environment present within cellular endosomes. Such internalizing peptides can be used to facilitate transport of SMNΔ7-degron or SMNΔ7$^{S270A}$ peptides and peptidomimetics, taken up by an endoeytic mechanism, from endosomal compartments to the cytoplasm.

A preferred pH-dependent membrane-binding internalizing peptide includes a high percentage of helix-forming residues, such as glutamate, methionine, alanine and leucine. In addition, a preferred internalizing peptide sequence includes ionizable residues having pKa's within the range of pH 5-7, so that a sufficient uncharged membrane-binding domain will be present within the peptide at pH 5 to allow insertion into the target cell membrane.

A particularly preferred pH-dependent membrane-binding internalizing peptide in this regard is aa1-aa2-aa3-EAALA (EALA)4-EALEALAA-1-amide (SEQ ID NO. 23), which represents a modification of the peptide sequence of Subbarao et al. (Biochemistry 26:2964, 1987). Within this peptide sequence, the first amino acid residue (aa1) is preferably a unique residue, such as cysteine or lysine, that facilitates chemical conjugation of the internalizing peptide to a targeting protein conjugate. Amino acid residues 2-3 may be selected to modulate the affinity of the internalizing peptide for different membranes. For instance, if both residues 2 and 3 are lys or arg, the internalizing peptide will have the capacity to bind to membranes or patches of lipids having a negative surface charge. If residues 2-3 are neutral amino acids, the internalizing peptide will insert into neutral membranes.

Yet other preferred internalizing peptides include peptides of apo-lipoprotein A-1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary internalizing peptides may be modified through attachment of substituents that enhance the alpha-helical character of the internalizing peptide at acidic pH.

Yet another class of internalizing peptides suitable for use within the present invention include hydrophobic domains that are "hidden" at physiological pH, but are exposed in the low pH environment of the target cell endosome. Upon pH-induced unfolding and exposure of the hydrophobic domain, the moiety binds to lipid bilayers and effects translocation of the covalently linked polypeptide into the cell cytoplasm. Such internalizing peptides may be modeled after sequences identified in, e.g., *Pseudomonas* exotoxin A, clathrin, or Diphtheria toxin.

Pore-forming proteins or peptides may also serve as internalizing peptides herein. Pore-forming proteins or peptides may be obtained or derived from, for example, C9 complement protein, cytolytic T-cell molecules or NK-cell molecules. These moieties are capable of forming ring-like structures in membranes, thereby allowing transport of attached polypeptide through the membrane and into the cell interior.

Mere membrane intercalation of an internalizing peptide may be sufficient for translocation of the SMNΔ7-degron or SMNΔ7$^{S270A}$ peptide or peptidomimetic, across cell membranes. However, translocation may be improved by attaching to the internalizing peptide a substrate for intracellular enzymes (i.e., an "accessory peptide"). It is preferred that an accessory peptide be attached to a portion(s) of the internalizing peptide that protrudes through the cell membrane to the cytoplasmic face. The accessory peptide may be advantageously attached to one terminus of a translocating/internalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

An exemplary accessory moiety in this regard would be a peptide substrate for N-myristoyl transferase, such as GNAAAARR (SEQ ID NO. 24) (Eubanks et al., in: Peptides, Chemistry and Biology, Garland Marshall (ed.), ESCOM, Leiden, 1988, pp. 566-69) In this construct, an internalizing peptide would be attached to the C-terminus of the accessory peptide, since the N-terminal glycine is critical for the accessory moiety's activity. This hybrid peptide, upon attachment to an E2 peptide or peptidomimetic at its C-terminus, is N-myristylated and further anchored to the target cell membrane, e.g., it serves to increase the local concentration of the peptide at the cell membrane.

To further illustrate use of an accessory peptide, a phosphorylatable accessory peptide is first covalently attached to the C-terminus of an internalizing peptide and then incorporated into a fusion protein with a SMNΔ7-degron or SMNΔ7$^{S270A}$ peptide or peptidomimetic. The peptide component of the fusion protein intercalates into the target cell plasma membrane and, as a result, the accessory peptide is translocated across the membrane and protrudes into the cytoplasm of the target cell. On the cytoplasmic side of the plasma membrane, the accessory peptide is phosphorylated by cellular kinases at neutral pH. Once phosphorylated, the accessory peptide acts to irreversibly anchor the fusion protein into the membrane. Localization to the cell surface membrane can enhance the translocation of the polypeptide into the cell cytoplasm.

Suitable accessory peptides include peptides that are kinase substrates, peptides that possess a single positive charge, and peptides that contain sequences which are glycosylated by membrane-bound glycotransferases: Accessory peptides that are glycosylated by membrane-bound glycotransferases may include the sequence x-NLT-x, where "x" may be another peptide, an amino acid, coupling agent or hydrophobic molecule, for example. When this hydrophobic tripeptide is incubated with microsomal vesicles, it crosses vesicular membranes, is glycosylated on the luminal side, and is entrapped within the vesicles due to its hydrophilicity (C. Hirschberg et al., (1987) Ann. Rev. Biochem. 56:63-87). Accessory peptides that contain the sequence x-NLT-x thus will enhance target cell retention of corresponding polypeptide.

In another embodiment of this aspect of the invention, an accessory peptide can be used to enhance interaction of the SMNΔ7-degron or SMNΔ7$^{S270A}$ peptide or peptidomimetic with the target cell. Exemplary accessory peptides in this regard include peptides derived from cell adhesion proteins containing the sequence "RGD", or peptides derived from laminin containing the sequence CDPGYIGSRC (SEQ ID NO. 25). Extracellular matrix glycoproteins, such as fibronectin and laminin, bind to cell surfaces through receptor-mediated processes. A tripeptide sequence, RGD, has been identified as necessary for binding to cell surface receptors. This sequence is present in fibronectin, vitronectin, C3bi of complement, von-Willebrand factor, EGF receptor, transforming growth factor beta, collagen type 1, lambda receptor of E. Coli, fibrinogen and Sindbis coat protein (E. Ruoslahti, Ann. Rev. Biochem. 57:375413, 1988). Cell surface receptors that recognize RGD sequences have been grouped into a superfamily of related proteins designated "integrins". Binding of "RGD peptides" to cell surface integrins will promote cell-surface retention, and ultimately translocation, of the polypeptide.

As described above, the internalizing and accessory peptides can each, independently, be added to the SMNΔ7-degron or SMNΔ7$^{S270A}$ peptide or peptidomimetic by either chemical cross-linking or in the form of a fusion protein. In the instance of fusion proteins, unstructured polypeptide linkers can be included between each of the peptide moieties.

In general, the internalization peptide will be sufficient to also direct export of the polypeptide. However, where an accessory peptide is provided, such as an RGD sequence, it may be necessary to include a secretion signal sequence to direct export of the fusion protein from its host cell. In preferred embodiments, the secretion signal sequence is located at the extreme N-terminus, and is (optionally) flanked by a proteolytic site between the secretion signal and the rest of the fusion protein.

In certain instances, it may also be desirable to include a nuclear localization signal as part of the SMNΔ7-degron or SMNΔ7$^{S270A}$ peptide.

In the generation of fusion polypeptides including the subject SMNΔ7-degron or SMNΔ7$^{S270A}$ peptides, it may be necessary to include unstructured linkers in order to ensure proper folding of the various peptide domains. Many synthetic and natural linkers are known in the art and can be adapted for use in the present invention, including the (Gly$_3$Ser)$_4$ linker.

(e) SMNΔ7-Degron or SMNΔ7$^{S270A}$ Mimetics

In other embodiments, the subject SMNΔ7-degron or SMNΔ7$^{S270A}$ therapeutics are peptidomimetics of the SMNΔ7-degron or SMNΔ7$^{S270A}$ peptides. Peptidomimetics are compounds based on, or derived from, peptides and proteins. The SMNΔ7-degron or SMNΔ7$^{S270A}$ peptidomimetics of the present invention typically can be obtained by structural modification of a known SMNΔ7-degron or SMNΔ7$^{S270A}$ peptide sequence using unnatural amino acids, conformational restraints, isosteric replacement, and the like. The subject peptidomimetics constitute the continuum of structural space between peptides and non-peptide synthetic structures; SMNΔ7-degron or SMNΔ7$^{S270A}$ peptidomimetics may be useful, therefore, in delineating pharmacophores and in helping to translate peptides into nonpeptide compounds with the activity of the parent SMNΔ7-degron or SMNΔ7$^{S270A}$ peptides.

Moreover, as is apparent from the present disclosure, mimetopes of the subject SMNΔ7-degron or SMNΔ7$^{S270A}$ peptides can be provided. Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p 123), C-7 mimics (Huffman et al. in Peptides: Chemistry and Biologyy, G. R. Marshall ed., ESCOM Publisher: Leiden, Netherlands, 1988, p. 105), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), β-aminoalcohols (Gordon et al. (1985) Biochem Biophys Res Commun 126:419; and Dann et al. (1986) Biochem Biophys Res Commun 134:71), diaminoketones (Natarajan et al. (1984) Biochem Biophys Res Commun 124: 141), and methyleneamino-modified (Roark et al. in Peptides: Chemistry and Biology, G. R. Marshall ed., ESCOM Publisher: Leiden, Netherlands, 1988, p 134). Also, see generally, Session Analytic and synthetic methods, in in Peptides: Chemistry and Biology, G. R. Marshall ed., ESCOM Publisher: Leiden, Netherlands, 1988)

In addition to a variety of sidechain replacements which can be carried out to generate the SMNΔ7-degron or SMNΔ7$^{S270A}$ peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

Moreover, other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of binding to the SMNΔ7-degron or SMNΔ7$^{S270A}$ peptide. A mimetope can also be obtained, for example, from libraries of natural and synthetic compounds, in particular, chemical or combinatorial libraries (i.e., libraries of compounds that differ in sequence or size but that have the same building blocks). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling, the predicted mimetope structures can then be produced by, for example, chemical synthesis, recombinant DNA technology, or by isolating a mimetope from a natural source (e.g., plants, animals, bacteria and fungi).

A CPD SMNΔ7-degron or SMNΔ7$^{S270A}$, or chimeric protein of the invention may be synthesized by conventional techniques. For example, the peptides or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, 2$^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis.) By way of example, a CPD motif, CPD peptide, CPD motif binding partner, or chimeric protein may be synthesized using 9-fluorenyl methoxycarbonyl (Fmoc) solid phase chemistry with direct incorporation of phosphothreonine as the N-fluorenyl-methoxy-carbonyl-O-benzyl-L-phosphothreonine derivative.

N-terminal or C-terminal fusion proteins comprising a SMNΔ7-degron or SMNΔ7$^{S270A}$, or chimeric protein of the invention conjugated with other molecules may be prepared by fusing, through recombinant techniques, the N-terminal or C-terminal of the SMNΔ7-degron or SMNΔ7$^{S270A}$, or chimeric protein, and the sequence of a selected protein or selectable marker with a desired biological function. The resultant fusion proteins contain the SMNΔ7-degron or SMNΔ7$^{S270A}$, or chimeric protein fused to the selected protein or marker protein as described herein. Examples of proteins which may be used to prepare fusion proteins include immunoglobulins, glutathione-S-transferase (GST), hemagglutinin (HA), and truncated myc.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708, 871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, mane acid, tartaric acid, citric acid, benzoic acid, salicylic acid, benzenesulfonic acid, and toluenesulfonic acids.

2. Antibodies

The invention also contemplates antibodies specific for a SMNΔ7-degron or SMNΔ7$^{S270A}$, or chimeric protein of the invention. The antibodies may be intact monoclonal or polyclonal antibodies, and immunologically active fragments (e.g. a Fab or (Fab)$_2$ fragment), an antibody heavy chain, an antibody light chain, humanized antibodies, a genetically engineered single chain F.sub.V molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art.

Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin and thyroglobulin, keyhole limpet hemocyanin. The coupled polypeptide may then be used to immunize the animal (e.g., a mouse, a rat, or a rabbit).

A SMNΔ7-degron or SMNΔ7$^{S270A}$, or chimeric protein, and antibodies specific for same may be labeled using conventional methods with various enzymes, fluorescent materials, luminescent materials and radioactive materials. Suitable enzymes, fluorescent materials, luminescent materials, and radioactive material are well known to the skilled artisan. Labeled antibodies specific for the peptides of the invention may be used to screen for proteins with a SMNΔ7-degron or SMNΔ7$^{S270A}$ peptide sequence or may be used to screen for proteins containing binding sites for a SMNΔ7-degron or SMNΔ7$^{S270A}$ protein (e.g. binding partners).

B. Nucleic Acids

In one embodiment, the invention includes an isolated nucleic acid comprising a nucleotide sequence encoding a SMNΔ7-degron peptide. In a particular embodiment, the isolated nucleotide sequence comprises SEQ ID NO. 3, SEQ ID NO. 5, or SEQ ID No. 14.

In another embodiment, the invention includes an isolated nucleic acid comprising a nucleotide sequence encoding SEQ ID NO. 4, SEQ ID NO. 6, SEQ ID NO. 7, SEQ ID NO. 9, SEQ ID NO. 10, SEQ ID NO. 11, SEQ ID NO. 12, or SEQ ID NO. 13.

In another embodiment, the invention includes an isolated nucleic acid comprising a nucleotide sequence that encodes a SMNΔ7$^{S270A}$ peptide (SEQ ID NO. 8).

The nucleotide sequences encoding a SMNΔ7-degron peptide or a SMNΔ7$^{S270A}$ peptide can alternatively comprise sequence variations with respect to the original nucleotide sequences, for example, substitutions, insertions and/or deletions of one or more nucleotides, with the condition that the resulting polynucleotide encodes a polypeptide according to the invention. Therefore, the scope of the present invention includes nucleotide sequences that are substantially homologous to the nucleotide sequences recited herein and encodes a SMNΔ7-degron peptide or a SMNΔ7$^{S270A}$ peptide.

In the sense used in this description, a nucleotide sequence is "substantially homologous" to any of the nucleotide sequences describe herein when its nucleotide sequence has a degree of identity with respect to the nucleotide sequence of at least 60%, advantageously of at least 70%, preferably of at least 85%, and more preferably of at least 95%. A nucleotide sequence that is substantially homologous to a nucleotide sequence encoding a SMNΔ7-degron peptide or a SMNΔ7$^{S270A}$ peptide can typically be isolated from a producer organism of the polypeptide of the invention based on the information contained in the nucleotide sequence by means of introducing conservative or non-conservative substitutions, for example. Other examples of possible modifications include the insertion of one or more nucleotides in the sequence, the addition of one or more nucleotides in any of the ends of the sequence, or the deletion of one or more nucleotides in any end or inside the sequence. The degree of identity between two polynucleotides is determined using computer algorithms and methods that are widely known for the persons skilled in the art. The identity between two amino acid sequences is preferably determined by using the BLASTN algorithm [BLAST Manual, Altschul, S., et al., NCBI NLM NIH Bethesda, Md. 20894, Altschul, S., et al., J. Mal. Biol. 215: 403-410 (1990)].

In another aspect, the invention relates to a construct, comprising a nucleotide sequence encoding a SMNΔ7-degron peptide, a derivative thereof, or a SMNΔ7$^{S270A}$ peptide. In a particular embodiment, the construct is operatively bound to transcription, and optionally translation, control elements. The construct can incorporate an operatively bound regulatory sequence of the expression of the nucleotide sequence of the invention, thus forming an expression cassette.

A SMNΔ7-degron, a derivative thereof, or SMNΔ7$^{S270A}$ or chimeric protein may be prepared using recombinant DNA methods. Accordingly, nucleic acid molecules which encode a SMNΔ7-degron, a derivative thereof, or SMNΔ7$^{S270A}$, or chimeric protein may be incorporated in a known manner into an appropriate expression vector which ensures good expression of the SMNΔ7-degron, a derivative thereof, or SMNΔ7$^{S270A}$, or chimeric protein.

Therefore, in another aspect, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

Vectors suitable for the insertion of the polynucleotides are vectors derived from expression vectors in prokaryotes such as pUC18, pUC19, Bluescript and the derivatives thereof, mp18, mp19, pBR322, pMB9, ColE1, pCR1, RP4, phages and "shuttle" vectors such as pSA3 and pAT28, expression vectors in yeasts such as vectors of the type of 2 micron plasmids, integration plasmids, YEP vectors, centromere plasmids and the like, expression vectors in insect cells such as vectors of the pAC series and of the pVL, expression vectors in plants such as pIBI, pEarleyGate, pAVA, pCAMBIA, pGSA, pGWB, pMDC, pMY, pORE series and the like, and expression vectors in eukaryotic cells based on viral vectors (adenoviruses, viruses associated to adenoviruses such as retroviruses and, particularly, lentiviruses) as well as non-viral vectors such as pSilencer 4.1-CMV (Ambion), peDNA3, pcDNA3.1/hyg, pHMCV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and PKSV-10, pBPV-1, pML2d and pTDT1.

By way of illustration, the vector in which the nucleic acid sequence is introduced can be a plasmid which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al., "Molecular cloning, a Laboratory Manual", 2nd ed., Cold Spring Harbor Laboratory Press, N.Y., 1989 Vol 1-3]. In a particular embodiment, the vector is a vector useful for transforming animal cells.

The recombinant expression vectors may also contain nucleic acid molecules which encode a portion which provides increased expression of the recombinant SMNΔ7-degron, a derivative thereof, or SMNΔ7$^{S270A}$, or chimeric protein; increased solubility of the recombinant SMNΔ7-degron or SMNΔ7$^{S270A}$, or chimeric protein; and/or aid in the purification of the recombinant SMNΔ7-degron, a derivative thereof, or SMNΔ7$^{S270A}$, or chimeric protein by acting as a ligand in affinity purification. For example, a proteolytic cleavage site may be inserted in the recombinant peptide to allow separation of the recombinant CPD SMNΔ7-degron, derivative thereof, or SMNΔ7$^{S270A}$, or chimeric protein from the fusion portion after purification of the fusion protein. Examples of fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCRT™, in connection with the compositions disclosed herein (U.S. Pat. No. 4,683,202, U.S. Pat. No. 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2001). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In a particular embodiment, the expression of the nucleic acid is externally controlled. In a more particular embodiment, the expression is externally controlled using the doxycycline Tet-On system.

The recombinant expression vectors may also contain a selectable marker gene which facilitates the selection of transformed or transfected host cells. Suitable selectable marker genes are genes encoding proteins such as 6418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. The selectable markers may be introduced on a separate vector from the nucleic acid of interest.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479: 79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Recombinant expression vectors may be introduced into host cells to produce a recombinant cell. The cells can be prokaryotic or eukaryotic. The vector of the invention can be used to transform eukaryotic cells such as yeast cells, *Saccharomyces cerevisiae*, or mammal cells for example epithelial kidney 293 cells or U2OS cells, or prokaryotic cells such as bacteria, *Escherichia coli* or *Bacillus subtilis*, for example. Nucleic acid can be introduced into a cell using conventional techniques such as calcium phosphate or calcium chloride co-precipitation, DEAE-dextran-mediated transfection, lipofectin, electroporation or microinjection. Suitable methods for transforming and transfecting host cells may be found in Sambrook et al. (Molecular Cloning: A Laboratory Manual, 2nd Edition, Cold Spring Harbor Laboratory press (1989)), and other laboratory textbooks.

For example, a SMNΔ7-degron or SMNΔ7$^{S270A}$, or chimeric protein of the invention may be expressed in bacterial cells such as E, coli, insect cells (using baculovirus), yeast cells or mammalian cells. Other suitable host cells can be found in Goeddel, Gene Expression Technology: Methods in Enzymology 185, Academic Press, San Diego, Calif. (1991).

Transgenic Mammal

The nucleotide sequences, vectors or cells described above can be used to obtain a transgenic non-human mammal having, inserted in the genome thereof, the nucleotide sequence of the polypeptides of the invention together with the regulatory sequences thereof.

Therefore, in another aspect, the invention relates to a mammal, comprising a nucleotide sequence of the invention, or a gene construct of the invention, or a vector of the invention, or a cell of the invention. In a particular embodiment of the invention, the mammal is preferably a rodent, more preferably a mouse or a rat. The non-human mammal of the invention can have any genetic background of those known in the state of the art by a person skilled in the art (Hogan et al., 1986, Manipulating the Mouse Embryo: A Laboratory Manual, Cold Spring Harbor, N.Y.).

C. Inhibitors of SMNΔ7-Degron Activity

In one embodiment, the invention includes an inhibitor of SMNΔ7-degron activity. An inhibitor of SMNΔ7-degron activity is any compound, molecule, or agent that prevents the degradation of a protein carrying the SMNΔ7-degron signal. Accordingly, a SMNΔ7-degron inhibitor will increase that expression, function, and stability of a protein. A SMNΔ7-degron inhibitor may be an siRNA, a ribozyme, an antisense, an aptamer, a peptidomimetic, a small molecule, or any combination thereof.

(1) siRNA

In one embodiment, siRNA is used to decrease the level of SMNΔ7-degron protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19):306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, Pa. (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, CIT content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of SMNΔ7-degron protein using RNAi technology.

In other related aspects, the invention includes an isolated nucleic acid encoding an inhibitor, wherein an inhibitor such as an siRNA or antisense molecule, inhibits SMNΔ7-degron, a derivative thereof, a regulator thereof, or a downstream effector, operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning; A Laboratory Manual, Cold Spring Harbor Laboratory, New York), and in Ausubel et al. (1997, Current Protocols in Molecular Biology, John Wiley & Sons, New York) and as described elsewhere herein. In another aspect of the invention, SMNΔ7-degron, or a regulator thereof, can be inhibited by way of inactivating and/or sequestering SMNΔ7-degron, or a regulator thereof. As such, inhibiting the effects of SMNΔ7-degron can be accomplished by using a transdominant negative mutant.

In another aspect, the invention includes a vector comprising an siRNA or antisense polynucleotide. Preferably, the siRNA or antisense polynucleotide is capable of inhibiting the expression of a target polypeptide, wherein the target polypeptide is selected from the group consisting of SMNΔ7-degron, a downstream effector, or regulators thereof. The incorporation of a desired polynucleotide into a vector and the choice of vectors is well-known in the art as described in, for example, Sambrook et al., supra, and Ausubel et al., supra, and elsewhere herein.

The siRNA or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA or antisense polynucleotide, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Modification of siRNA

Following the generation of the siRNA polynucleotide, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987 Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sol. 14:97-100; Stein, In: Oligodeoxynucleotides. Antisense Inhibitors of Gene Expression, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

(2) Antisense Nucleic Acids

In one embodiment of the invention, an antisense nucleic acid sequence which is expressed by a plasmid vector is used to inhibit SMNΔ7-degron, or a SMNΔ7-degron downstream effector expression. The antisense expressing vector is used to transfect a mammalian cell or the mammal itself, thereby causing reduced endogenous expression of SMNΔ7-degron, or downstream effector.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific in RNA molecule (Weintraub, 1990, Scientific American 262: 40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal, Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Compositions and methods for the synthesis and expression of antisense nucleic acids are as described elsewhere herein.

(3) Ribozymes

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target in RNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

In one embodiment of the invention, a ribozyme is used to inhibit SMNΔ7-degron, or a SMNΔ7-degron downstream effector expression. Ribozymes useful for inhibiting the expression of a target molecule may be designed by incorporating target sequences into the basic ribozyme structure which are complementary, for example, to the mRNA sequence of SMNΔ7-degron of the present invention. Ribozymes targeting SMNΔ7-degron or a downstream effector thereof, may be synthesized using commercially available reagents (Applied Biosystems, Inc., Foster City, Calif.) or they may be genetically expressed from DNA encoding them.

(4) Small Molecules

When the SMNΔ7-degron inhibitor is a small molecule, a small molecule agonist may be obtained using standard methods known to the skilled artisan. Such methods include chemical organic synthesis or biological means. Biological means include purification from a biological source, recombinant synthesis and in vitro translation systems, using methods well known in the art.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discover vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

II. Methods

A. Methods of Inhibiting SMNΔ7-Degron Activity

SMNΔ7-degron activity can be inhibited using any method known to the skilled artisan. Examples of methods to inhibit SMNΔ7-degron activity, include but are not limited to, inhibiting expression of an endogenous SMNΔ7-degron gene, decreasing expression of SMNΔ7-degron mRNA, and inhibiting the function, activity, or stability of a SMNΔ7-degron protein. A SMNΔ7-degron inhibitor may therefore be a compound that decreases expression of a SMNΔ7-degron gene, decreases SMNΔ7-degron in RNA half-life, stability and/or expression, or inhibits SMNΔ7-degron protein function, activity or stability. A SMNΔ7-degron inhibitor may be any type of compound, including but not limited to, a polypeptide, a nucleic acid, an aptamer, a peptidometic, and a small molecule, or combinations thereof.

SMNΔ7-degron inhibition may be accomplished either directly or indirectly. For example, SMNΔ7-degron may be directly inhibited by compounds or compositions that directly interact with SMNΔ7-degron protein, such as antibodies. Alternatively, SMNΔ7-degron may be inhibited indirectly by compounds or compositions that inhibit SMNΔ7-degron downstream effectors, or upstream regulators which up-regulate SMNΔ7-degron expression.

Decreasing expression of an endogenous SMNΔ7-degron gene includes providing a specific inhibitor of SMNΔ7-degron gene expression. Decreasing expression of SMNΔ7-degron mRNA or SMNΔ7-degron protein includes decreasing the half-life or stability of SMNΔ7-degron mRNA or decreasing expression of SMNΔ7-degron mRNA. Methods of decreasing expression of SMNΔ7-degron include, but are not limited to, methods that use an siRNA, a microRNA, an antisense nucleic acid, a ribozyme, an expression vector encoding a transdominant negative mutant, a peptide, a small molecule, other specific inhibitors of SMNΔ7-degron gene, mRNA, and protein expression, and combinations thereof.

B. Assays for Identifying and Testing Candidate Inhibitors of SMNΔ7-Degron

SMNΔ7-degron inhibitors can be identified by screening test compounds for their capacity to reduce or preclude SMNΔ7-degron gene expression, SMNΔ7-degron mRNA expression, or SMNΔ7-degron protein activity, function or stability in a cell. The SMNΔ7-degron coding sequence (SEQ ID NO: 6) in such screening assays may include an in-frame fusion of a tag to the SMNΔ7-degron coding sequence. Such tags enable monitoring of SMNΔ7-degron expression by antibody detection of the tags or spectral methods of detection (e.g., fluorescence or luminescence).

Accordingly, SMNΔ7-degron expression may be detected at either the protein or nucleic acid level. The invention should not be limited to any one method of protein or nucleic acid detection method recited herein, but rather should encompass all known or heretofor unknown methods of detection as are, or become, known in the art.

In one embodiment, antibodies specific for SMNΔ7-degron protein are used to detect SMNΔ7-degron protein expression in a sample, where a sample may be a cell, a culture solution, or a body sample. The method contacting the sample with at least one antibody directed to a SMNΔ7-degron protein to determine if the expression of the SMNΔ7-degron protein in the sample. Expression levels of the protein may be quantified using techniques well known in the art, including but not limited to densitometry. One of skill in the art will recognize that the immunocytochemistry method described herein below is performed manually or in an automated fashion.

Techniques for detecting antibody binding are well known in the art. Antibody binding to a SMNΔ7-degron protein may be detected through the use of chemical reagents that generate a detectable signal that corresponds to the level of antibody binding and, accordingly, to the level of SMNΔ7-degron protein expression. In one of the preferred immunocytochemistry methods of the invention, antibody binding is detected through the use of a secondary antibody that is conjugated to a labeled polymer. Examples of labeled polymers include but are not limited to polymer-enzyme conjugates. The enzymes in these complexes are typically used to catalyze the deposition of a chromogen at the antigen-antibody binding site, thereby resulting in cell staining that corresponds to expression level of the SMNΔ7-degron protein. Enzymes of particular interest include horseradish peroxidase (HRP) and alkaline phosphatase (AP). Commercial antibody detection systems, such as, for example the Dako Envision+ system (Dako North America, Inc., Carpinteria, Calif.) and Mach 3 system (Biocare Medical, Walnut Creek, Calif.), may be used to practice the present invention.

Detection of antibody binding can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

Immunoassays, in their simplest and most direct sense, are binding assays. Certain preferred immunoassays are the various types of enzyme linked immunosorbent assays (ELISA) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, antibodies binding to the SMNΔ7-degron protein are immobilized onto a selected surface exhibiting protein affinity, such as a well in a polystyrene microtiter plate. Then, a test sample is added to the wells. After binding and washing to remove non-specifically bound immunecomplexes, the bound antibody may be detected. Detection is generally achieved by the addition of a second antibody specific for the SMNΔ7-degron protein, that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the SMNΔ7-degron protein antigen are immobilized onto the well surface and then contacted with the antibodies of the invention. After binding and washing to remove non-specifically bound immunecomplexes, the bound antigen is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the SMNΔ7-degron protein is immobilized, involves the use of antibody competition in the detection. In this ELISA, labeled antibodies are added to the wells, allowed to bind to the SMNΔ7-degron protein, and detected by means of their label. The amount of marker antigen in an unknown sample is then determined by mixing the sample with the labeled antibodies before or during incubation with coated wells. The presence of SMNΔ7-degron protein antigen in the sample acts to reduce the amount of antibody available for binding to the well and thus reduces the ultimate signal.

Irrespective of the format employed, ELISAs have certain features in common, such as coating, incubating or binding, washing to remove non-specifically bound species, and detecting the bound immunecomplexes. These are described as follows.

In coating a plate with either antigen or antibody, the wells of the plate are incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating of nonspecific adsorption sites on the immobilizing surface reduces the background caused by nonspecific binding of antisera to the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control and/or biological sample to be tested under conditions effective to allow immunocomplex (antigen/antibody) formation. Detection of the immunecomplex then requires a labeled secondary binding ligand or antibody, or a secondary binding ligand or antibody in conjunction with a labeled tertiary antibody or third binding ligand.

"Under conditions effective to allow immunecomplex (antigen/antibody) formation" means that the conditions preferably include diluting the antigens and antibodies with solutions such as, but not limited to, BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this label is an enzyme that generates a color or other detectable signal upon incubating with an appropriate chromogenic or other substrate. Thus, for example, the first or second immunecomplex can be detected with a urease, glucose oxidase, alkaline phosphatase or hydrogen peroxidase-conjugated antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the ease of peroxidase as the enzyme label. Quantitation is then achieved by measuring the degree of color generation, e.g., using a visible spectra spectrophotometer.

Nucleic Acid-Based Techniques

In other embodiments, the expression of SMNΔ7-degron is detected at the nucleic acid level. Nucleic acid-based techniques for assessing expression are well known in the art and include, for example, determining the level of SMNΔ7-degron mRNA in a body sample. Many expression detection methods use isolated RNA. Any RNA isolation technique that does not select against the isolation of mRNA can be utilized for the purification of RNA from body samples (see, e.g., Ausubel, ed., 1999, Current Protocols in Molecular Biology (John Wiley & Sons, New York). Additionally, large numbers of tissue samples can readily be processed using techniques well known to those of skill in the art, such as, for example, the single-step RNA isolation process of Chomczynski, 1989, U.S. Pat. No. 4,843,155).

The term "probe" refers to any molecule that is capable of selectively binding to a specifically intended target biomolecule, for example, a nucleotide transcript or a protein encoded by or corresponding to a SMNΔ7-degron. Probes can be synthesized by one of skill in the art, or derived from appropriate biological preparations. Probes may be specifically designed to be labeled with a detectable label. Examples of molecules that can be used as probes include, but are not limited to, RNA, DNA, proteins, antibodies, and organic molecules.

Isolated mRNA can be detected in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a SMNΔ7-degron or a protein comprising a SMNΔ7-degron. Hybridization of an mRNA with the probe indicates that the SMNΔ7-degron in question is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array (Santa Clara, Calif.). A skilled artisan can readily adapt known mRNA detection methods for use in detecting the level of mRNA encoding the SMNΔ7-degron.

An alternative method for determining the level of SMNΔ7-degron mRNA in a sample involves the process of nucleic acid amplification, e.g., by RT-PCR (the experimental embodiment set forth in Mullis, 1987, U.S. Pat. No. 4,683, 202), ligase chain reaction (Barany, 1991, Proc. Natl. Acad. Sci. USA, 88:189 193), self sustained sequence replication (Guatelli, 1990, Proc. Natl. Acad. Sci. USA, 87:1874 1878), transcriptional amplification system (Kwok, 1989, Proc. Natl. Acad. Sci. USA, 86:1173 1177), Q-Beta Replicase (Lizardi, 1988, Bio/Technology, 6:1197), rolling circle replication (Lizardi, U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, SMNΔ7-degron expression is assessed by quantitative fluorogenic RT-PCR (i.e., the TaqMan™ System). Such methods typically use pairs of oligonucleotide primers that are specific for the SMNΔ7-degron. Methods for designing oligonucleotide primers specific for a known sequence are well known in the art.

SMNΔ7-degron expression levels of RNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of SMNΔ7-degron expression may also comprise using nucleic acid probes in solution.

SMNΔ7-degron activity results in increased degradation of the SMN protein in a cell. In one embodiment, an assay for identifying an SMNΔ7-degron inhibitor includes measuring and comparing SMN protein levels in a cell in the presence of a test compound, in the absence of the same test compound, or in the presence of a control such as a vehicle or a compound which is known not have any effect on SMNΔ7-degron activity. If the SMN protein level measured in a cell using techniques described elsewhere herein is greater in the presence of the test compound than in either its absence or in the presence of the control, than the test compound is identified as an SMNΔ7-degron inhibitor.

In another embodiment, an assay for identifying an SMNΔ7-degron inhibitor measures and compares cell viability in the presence of a test compound, in the absence of the same test compound, or in the presence of a control such as a vehicle or a compound which is known not have any effect on SMNΔ7-degron activity. If cell viability is enhanced in the presence of a test compound than in either its absence or in the presence of the control, than the test compound is identified as an SMNΔ7-degron inhibitor. Methods for assessing cell viability include, but are not limited to, morphological changes, such as pycnotic nuclei, uptake of dyes such as Hoechst dye and trypan blue exclusion. A commercially available kit, LIVE/DEAD cell viability/cytotoxicity kit (Invitrogen Molecular Probes, Carlsbad, Calif.), relies on a membrane permeant esterase substrate that, when cleaved by an esterase in live cells, yields a fluorescent signal.

In another embodiment of the invention, an in vitro binding assay is used to determine binding affinity and dissociation kinetics of potential SMNΔ7-degron inhibitors for SMNΔ7-degron or downstream effectors. Examples of in vitro binding assays are well known in the art. Standards may be used when testing new agents or compounds or when measuring the various parameters described herein. In addition, when measuring a parameter, measurement of a standard can include measuring parameters such as SMNΔ7-degron concentrations in a tissue or fluid obtained from a subject before the subject is treated with a test compound and the same parameters can be measured after treatment with the test compound. In another aspect of the invention, a standard can be an exogenously added standard which is an agent or compound that is added to a sample and is useful as an internal control, especially where a sample is processed through several steps or procedures and the amount of recovery of a marker of interest at each step must be determined. Such exogenously added internal standards are often added in a labeled form, i.e., a radioactive isotope.

Test compounds for use in such screening methods can be small molecules, nucleic acids including aptamers, peptides, peptidomimetics and other drugs. Peptide fragments of SMNΔ7-degron are contemplated that can competitively inhibit the binding of SMNΔ7-degron to a SMNΔ7-degron binding partner, thereby inhibiting SMNΔ7-degron activity. Peptide fragments of SMNΔ7-degron that include the known Arg-Gly-Asp (RGD) β1 integrin binding domain are preferred in the present invention.

The test compounds of the present invention can be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam, 1997, Anticancer Drug Des. 12:145). Inhibitors and activators of SMNΔ7-degron expression may be useful in therapeutic applications, or serve as lead drugs in the development of therapeutics. Synthetic techniques may be used to produce compounds, such as: chemical and enzymatic production of small molecules, peptides, nucleic acids, antibodies, and other therapeutic compositions useful in the practice of the methods of the invention. Other techniques may be used which are not described herein, but are known to those of skill in the art.

In one aspect of the invention libraries of small molecules, including but not limited to aptamers, peptidomimetics, SMNΔ7-degron peptide fragments, or peptidomimetics, may be assayed for competitive binding to SMNΔ7-degron binding partners.

SMNΔ7-degron inhibitors useful in the invention may be obtained using standard methods known to the skilled artisan. Such methods include chemical organic synthesis or biological means. Biological means include purification from a biological source, recombinant synthesis and in vitro translation systems, using methods well known in the art.

A peptide may be chemically synthesized by Merrifield-type solid phase peptide synthesis. This method may be routinely performed to yield peptides up to about 60-70 residues in length, and may, in some cases, be utilized to make peptides up to about 100 amino acids long. Larger peptides may also be generated synthetically via fragment condensation or native chemical ligation (Dawson et al., 2000, Ann. Rev. Biochem. 69:923-960).

Solid phase peptide synthesis is described by Stewart et al. in Solid Phase Peptide Synthesis, 2nd Edition, 1984, Pierce Chemical Company, Rockford, Ill.; and Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and coupling thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group, such as formation into a carbodiimide, a symmetric acid anhydride, or an "active ester" group, such as hydroxybenzotriazole or pentafluorophenyl esters.

Examples of solid phase peptide synthesis methods include the BOC method, which utilizes tert-butyloxycarbonyl as the α-amino protecting group, and the FMOC method, which utilizes 9-fluorenylmethyloxycarbonyl to protect the α-amino of the amino acid residues. Both methods are well-known by those of skill in the art.

Incorporation of N- and/or C-blocking groups may also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin, so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB (di vinyl benzene), resin, which upon hydrofluoric acid (HF) treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by trifluoroacetic acid (TFA) in dicholoromethane. Esterification of the suitably activated carboxyl function, e.g. with dicyclohexylcarbodiimide (DCC), can then proceed by addition of the desired alcohol, followed by de-protection and isolation of the esterified peptide product.

Incorporation of N-terminal blocking groups may be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product may then be cleaved from the resin, de-protected and subsequently isolated.

Prior to its use as a SMNΔ7-degron inhibitor, a peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate polypeptides based on their charge. Affinity chromatography is also useful in purification procedures.

Antibodies and peptides may be modified using ordinary molecular biological techniques to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The polypeptides useful in the invention may further be conjugated to non-amino acid moieties that are useful in their application. In particular, moieties that improve the stability, biological half-life, water solubility, and immunologic characteristics of the peptide are useful. A non-limiting example of such a moiety is polyethylene glycol (PEG).

The invention also contemplates the agents (e.g. motifs, peptides comprising the motifs, and peptide mimetics thereof) identified using this method of the invention. The agents (e.g. motifs, peptides comprising the motifs, and peptide mimetics thereof) may be used to modulate SMNΔ7-degron dependent protein degradation, and they may be used to modulate cellular processes of cells (such as proliferation, growth, and/or differentiation, in particular glucose and methionine biosynthesis, gene expression, cell division, and transcription) in which the agents are introduced. An agent may be used to disrupt SMNΔ7-degron-dependent degeneration of a regulatory protein (ie. stabilize a regulatory protein), or to selectively degrade a target protein, for instance by fusing the motif to a binding partner of the target protein.

Accordingly, the agents (e.g. motifs, peptides comprising the motifs, and peptide mimetics thereof) may be formulated into compositions for administration to individuals suffering from a disease, disorder, or condition related to SMNΔ7-degron activity, particularly SMA.

C. Methods of Treating SMA and SMNΔ7-Degron Related Disorders

The invention includes methods for the treatment of a SMNΔ7-degron related disorder. As used herein, the term "SMNΔ7-degron related disorder" refers to any disease, disorder, or condition which is caused or characterized by activity of SMNΔ7-degron, including SMN protein activity and mRNA metabolism. In one embodiment, the invention includes methods for the treatment of SMA.

Administration of a SMNΔ7-degron inhibitor comprising one or more peptides, a small molecule, an antisense nucleic acid, a soluble receptor, or an antibody in a method of treatment can be achieved in a number of different ways, using methods known in the art.

It will be appreciated that a SMNΔ7-degron inhibitor of the invention may be administered to a subject either alone, or in conjunction with another therapeutic agent. In one embodiment, the SMNΔ7-degron inhibitor is administered to a subject in combination with a proteasome inhibitor. Examples of a proteasome inhibitor include, but are not limited to, Bortezamib, PS-519, eponemycin, epoxomycin, aclacinomycin A, lactacystin, calpain inhibitor and derivatives thereof such as CEP-1612, MG132, benzamide, CVT-63417, and a series of dipeptide boronic acid inhibitors exemplified by PS-341.

In one embodiment, an exogenous SMNΔ7-degron inhibitor peptide is administered to a subject. The exogenous peptide may also be a hybrid or fusion protein to facilitate, for instance, delivery to target cells or efficacy. In one embodiment, a hybrid protein may comprise a tissue-specific targeting sequence.

The therapeutic and prophylactic methods of the invention thus encompass the use of pharmaceutical compositions comprising a SMNΔ7-degron inhibitory peptide, fusion protein, small molecule, soluble receptor, or antibody of the invention and/or an isolated nucleic acid encoding a SMNΔ7-degron inhibitory peptide, fusion protein small molecule, soluble receptor, or antibody of the invention to practice the methods of the invention. The pharmaceutical compositions useful for practicing the invention may be administered to deliver a dose of from ng/kg/day and 100 mg/kg/day. In one embodiment, the invention envisions administration of a dose which results in a concentration of the compound of the present invention from 1 μM and 10 μM in a mammal.

Typically, dosages which may be administered in a method of the invention to a mammal, preferably a human, range in amount from 0.5 μg to about 50 mg per kilogram of body weight of the mammal While the precise dosage administered will vary depending upon any number of factors, including but not limited to, the type of mammal and type of disease state being treated, the age of the mammal and the route of administration. Preferably, the dosage of the compound will vary from about 1 μg to about 10 mg per kilogram of body weight of the mammal. More preferably, the dosage will vary from about 3 μg to about 1 mg per kilogram of body weight of the mammal.

The compound may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

In a preferred embodiment, the invention includes methods for treating SMA by inhibiting the activity of SMNΔ7-degron. In one aspect, SMNΔ7-degron activity is inhibited by administering a SMNΔ7-degron inhibitor to a subject in order to inhibit the degradation of a protein. In one embodiment, a SMNΔ7-degron inhibitor is administered to a subject to inhibit the degradation of an SMN protein. In another aspect, SMNΔ7-degron activity may be inhibited by providing exogenous SMNΔ7$^{S270A}$.

The administration of the polypeptide of the invention to the subject having a SMNΔ7-degron related disorder may be accomplished using gene therapy. Gene therapy, which is based on inserting a therapeutic gene into a cell by means of an ex vivo or an in vivo technique. Suitable vectors and methods have been described for genetic therapy in vitro or in vivo, and are known as expert on the matter; see, for example, Giordano, Nature Medicine 2 (1996), 534-539; Schaper, Circ. Res 79 (1996), 911-919; Anderson, Science 256 (1992), 808-813; Isner, Lancet 348 (1996), 370-374; Muhlhauser, Circ. Res 77 (1995), 1077-1086; Wang, Nature Medicine 2 (1996), 714-716; WO94/29469; WO97/00957 or Schaper, Current Opinion in Biotechnology 7 (1996), 635-640 and the references quoted therein. The polynucleotide codifying the polypeptide of the invention can be designed for direct insertion or by insertion through Liposomes or viral vectors (for example, adenoviral or retroviral vectors) in the cell. Preferably the cell is a cell of the germinal line, an embryonic cell or egg cell or derived from the same, more preferably the cell is a core cell. Suitable gene distribution systems that can be used according to the invention may include liposomes, distribution systems mediated by receptor, naked DNA and viral vectors such as the herpes virus, the retrovirus, the adenovirus and adeno-associated viruses, among others. The distribution of nucleic acids to a specific site in the body for genetic therapy can also be achieved by using a biolistic distribution system, such as that described by Williams (Proc. Natl. Acad. Sei. USA, 88 (1991), 2726-2729). The standard methods for transfecting cells with recombining DNA are well known by an expert on the subject of molecular biology, see, for example, WO94/29469; see also supra. Genetic therapy can be carried out by directly administering the recombining DNA molecule or the vector of the invention to a patient or transfecting the cells with the polynucleotide or the vector of the invention ex vivo and administering the transfected cells to the patient.

III. Pharmaceutical Compositions

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Other active agents useful in the treatment of fibrosis include anti-inflammatories, including corticosteroids, and immunosuppressants.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Kits

The invention also includes a kit comprising a SMNΔ7-degron inhibitor and an instructional material which describes, for instance, administering the SMNΔ7-degron inhibitor to a subject as a prophylactic or therapeutic treatment as described elsewhere herein. In an embodiment, the kit further comprises a (preferably sterile) pharmaceutically acceptable carrier suitable for dissolving or suspending the therapeutic composition, comprising a SMNΔ7-degron inhibitor, for instance, prior to administering the inhibitor to a subject. Optionally, the kit comprises an applicator for administering the inhibitor. In one embodiment of the invention, the applicator is designed for pulmonary administration of the SMNΔ7-degron inhibitor. In another embodiment, the kit comprises an antibody that specifically binds an epitope on SMNΔ7-degron. Preferably, the antibody recognizes a human SMNΔ7-degron.

A kit comprising a nucleic acid encoding a peptide or antibody of the invention and an instructional material is also provided.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods employed in the experiments disclosed herein are now described.

Plasmid Construction and Generation of Mutations

To construct plasmids expressing Luc-fused proteins, the luciferase gene was cloned into pcDNA3.1 vector at HindIII/KpnI sites, then DNA fragments encoding full-length wild type human SMN, SMNΔ7, several deletion mutants of SMNΔ7, and optiPEST were inserted into the KpnI/XhoI sites. SMNΔ7 mutants with single amino acid change were generated by mutating residues in YG+EMLA to alanine by Quickchange site-directed mutagenesis kit (Stratagene).

Plasmid expressing GFP-YG+EMLA was constructed by inserting a DNA fragment encoding YG+EMLA into pEGFP vector (Clontech) at KpnI/BamHI sites. Plasmids expressing HA-SMNs were constructed by inserting DNA fragments encoding HA-tagged SMN, SMNΔ7, and SMNΔ7$^{SMA}$ into the BamHI/XhoI sites of pcDNA3 vector. To generate retroviral plasmids to express SMNs in S5 cells, DNA fragments encoding SMN, SMNΔ7, and SMNΔ7$^{S270A}$ were cloned into the EcoRI/XhoI sites of pMX vector as described in Wang et al., 2001, J. Biol. Chem. 276:9599, which is hereby incorporated in its entirety.

Assays for Protein Stability

Cells (293T cells) were transfected with plasmids expressing various constructs including Luc-SMN, Luc-SMNΔ7, GFP-YG+EMLA or GFP-NS. Forty-eight hours after transfection, the cells were treated with CHX (0.1 mg/ml) for various times as indicated and then assayed for luciferase activity. Luciferase activity at each time point was calculated by comparison to those at time 0, which was set to 100%. Luciferase activities were measured using One-Glo reagent (Promega).

Rescue of S5 Cell Viability

S5 cells were maintained and infected with retroviruses expressing SMN, SMNΔ7, and SMNΔ7$^{S270A}$ as described (Wang et al., 2001, J. Biol. Chem. 276:9599).

SMN Complex Activity Assay

Cytoplasmic extracts from rescued S5 cells were prepared and assayed for snRNP assembly in vitro as described in Wan et al., 2005, Mol. Cell. Biol. 25:5543, hereby incorporated in its entirety.

Antibodies

Mouse monoclonal antibodies, anti-SMN (62E7) and anti-Magoh (18G12), were used as previously described (Wan et al., 2005, Mol. Cell. Biol. 25:5543). Rabbit polyclonal antibodies used were anti-HA (Santa Cruz) and anti-GFP (Santa Cruz).

The results of the experiments presented in this Example are now described.

Example 1

Identification of a Protein Degradation Sequence on the C-Terminus of SMN

A reporter system that recapitulates the differential stability of full-length SMN and SMNΔ7 and allows quantitative assessment of SMNΔ7's instability determinants was developed. Luciferase reporter proteins consisting of normal SMN or SMNΔ7 fused to the carboxyl-terminus of luciferase (Luc) were produced by transfection of the corresponding cDNA constructs in 293T cells (FIG. 1). Forty-eight hours after transfection, cells were treated with the protein synthesis inhibitor cycloheximide (CHX), and luciferase activity was measured at time intervals of up to 10 hours. Consistent with previous reports (Lorson et al., 2000, Hum Mol Genet 9(2):259-65), SMN has a half-life ($t_{1/2}$) of >8 hours whereas SMNΔ7 has a $t_{1/2}$ of ~3 hours. After 10 hours of CHX chase there was 3 times more SMN than SMNΔ7.

Several constructs were prepared to determine the role of the carboxyl-terminal sequence of SMNΔ7 in this protein's instability. Deletion of the carboxyl terminal EMLA from SMNΔ7 (SMNΔ7ΔEMLA) increased the half-life of SMNΔ7 by 2-fold (FIG. 1), and a further deletion of the YG box (SMNΔ7ΔYG), a conserved tyrosine/glycine—rich motif in divergent SMNs (Talbot et al., 1997, Hum Mol Genet 6(3):497-500) that is essential for SMN oligomerization (Pellizzoni et al., 1999, Proc Natl Acad Sci USA 96(20):11167-72), also had the same effect. These results suggest that EMLA and the YG box are major contributors to SMNΔ7's instability. Importantly, YG+EMLA alone was sufficient to cause dramatic instability of Luc, which is similar to that of SMNΔ7. Neither YG nor EMLA alone was sufficient for full destabilization activity (FIG. 1). N-terminal deletions in the YG box decreased the destabilizing activity of YG+EMLA (data not shown). These data indicate that YG+EMLA, corresponding to SMNΔ7 amino acids 268-282, is the minimal sequence required for full SMNΔ7 destabilization and it is both necessary and sufficient to trigger rapid degradation of a heterologous protein.

Figure 2:
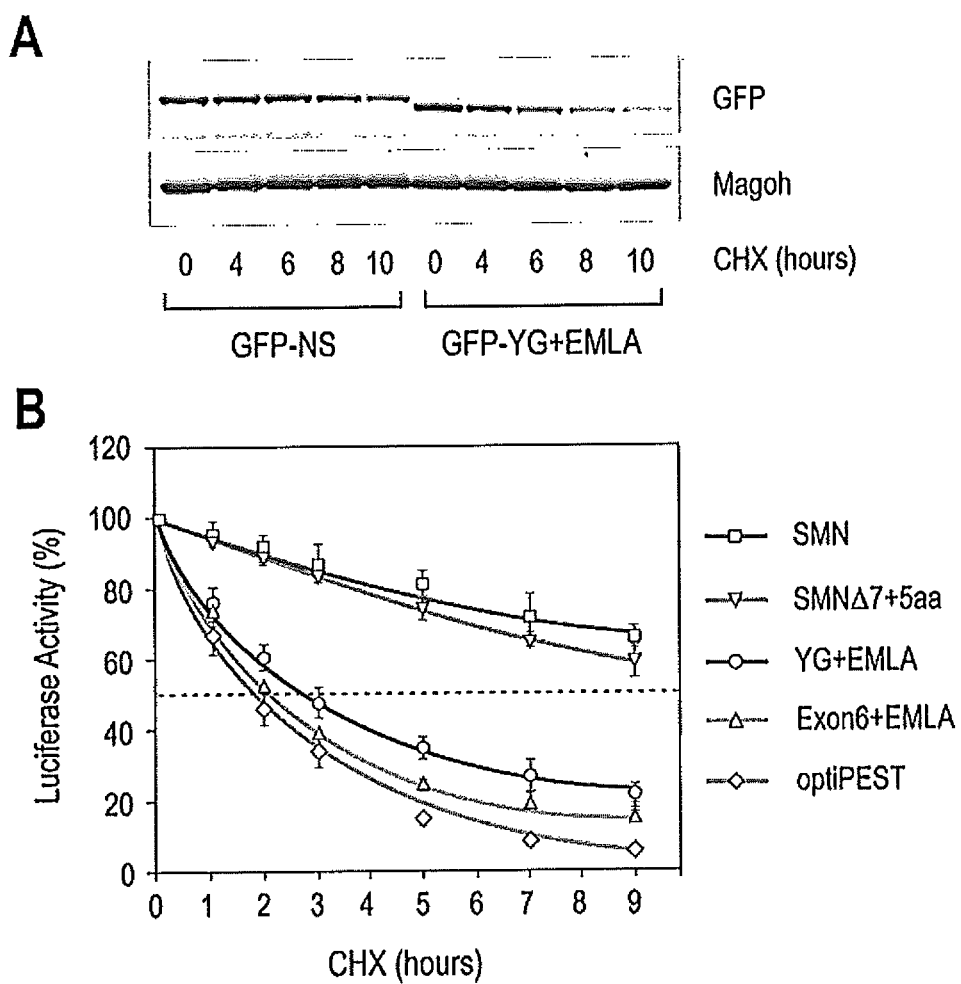
FIG. 2, comprising

As a further test of this conclusion, YG+EMLA was fused to another reporter, GFP, and expressed along with GFP as a control in 293T cells. The GFP signal from GFP-YG+EMLA, as determined by Western blots, showed a gradual decrease after treatment with CHX (FIG. 2A). GFP-YG+EMLA protein decreased faster than GFP-NS (nonspecific sequence), and the half-life ($t_{1/2}$) of GFP-YG+EMLA was about half of that of GFP-NS. These results suggest that YG+EMLA functions as a protein degradation sequence. For comparison, the destabilizing activity on the same reporter of YG+EMLA and an optimized PEST, a potent and well characterized protein destabilizing signal was tested (Li et al., 1998, J Biol Chem 273(52):34970-5). YG+EMLA had a similar effect to that of the genetically improved PEST (FIG. 2B).

Furthermore, SMN Exon6+EMLA, which is the same size as the 41 amino acid PEST sequence, conferred similar instability. As this optimized PEST sequence has about half the half-life of the natural one (Li et al., 1998, J Biol Chem 273(52):34970-5), YG+EMLA could be estimated to have similar or stronger destabilization activity than that of the natural PEST sequence and Exon6+EMLA is about twice as strong. These data demonstrate that YG+EMLA is a highly potent and transferable protein degradation signal (degron), which is designated SMNΔ7-DEG, for SMNΔ7 degron, herein. Addition of five amino acids to the C-terminal end of EMLA (SMNΔ7+5aa) caused SMNΔ7 stabilization, indicating that SMNΔ7-DEG must be exposed at the C-terminus of the protein for activity (FIG. 2B). This is consistent with the observations that additional several amino acids, which can be effected by aminoglycoside-forced translational readthrough, enhanced SMNΔ7 stability and functionality (Mattis et al., 2008, Neurosci Lett 442(1):54-8; Heier et al., 2009, Hum Mol Genet 18(7):1310-22).

Example 2

SMNΔ7 is Degraded by the Proteasome

Figure 5:
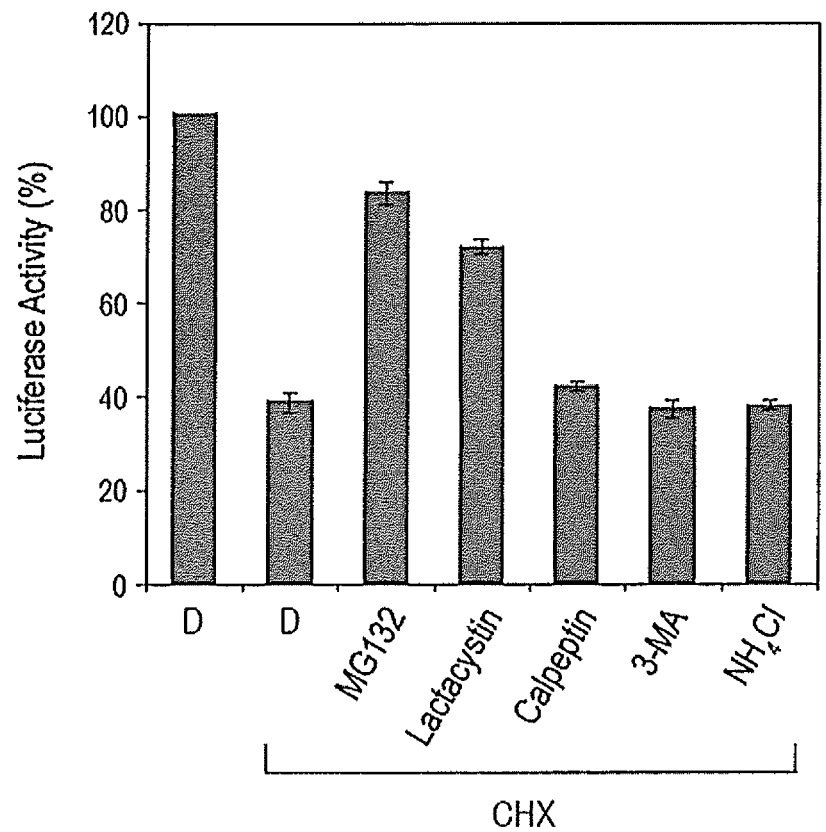
FIG. 5 is a graph depicting the effect of proteasome inhibitors on inhibiting SMNΔ7 degradation. Luciferase activity is measured after application of proteasome inhibitors (MG132 and Lactacystin), the calpain inhibitor (Calpeptin), the autophagy inhibitor (3-methyladenine; 3-MA), and the lysosomal inhibitor (ammonium chloride; NH$_4$Cl) in the presence of CHX for 5 hours. Error bars represent SDs from three independent experiments.

SMN was previously shown to be degraded by the proteasome (Burnett et al., 2009, Mol Cell Biol 29(5):1107-15; Chang et al., 2004, Neurochem. Int. 45(7):1107-12). To determine if SMNΔ7 is also degraded by this system, cells expressing Luc-SMNΔ7 were treated with proteasome inhibitors including MG132 and Lactaeystin, for 5 hours in the presence of CHX. CHX treatment alone resulted in a 60% decrease in signal, but a much smaller decrease was seen in the presence of proteasome inhibitors MG132 and Lactacystin (FIG. 5). Inhibitors of other proteolytic activities, such as lysosomal proteases, autophagy, and calpain (N1-1$_4$Cl, 3-methyladenine, and calpeptin, respectively) had no effect. These data demonstrate that SMNΔ7 is degraded by the proteasome.

Example 3

Identification of Key Residues for Conferring Degenerin Activity

Figure 3:
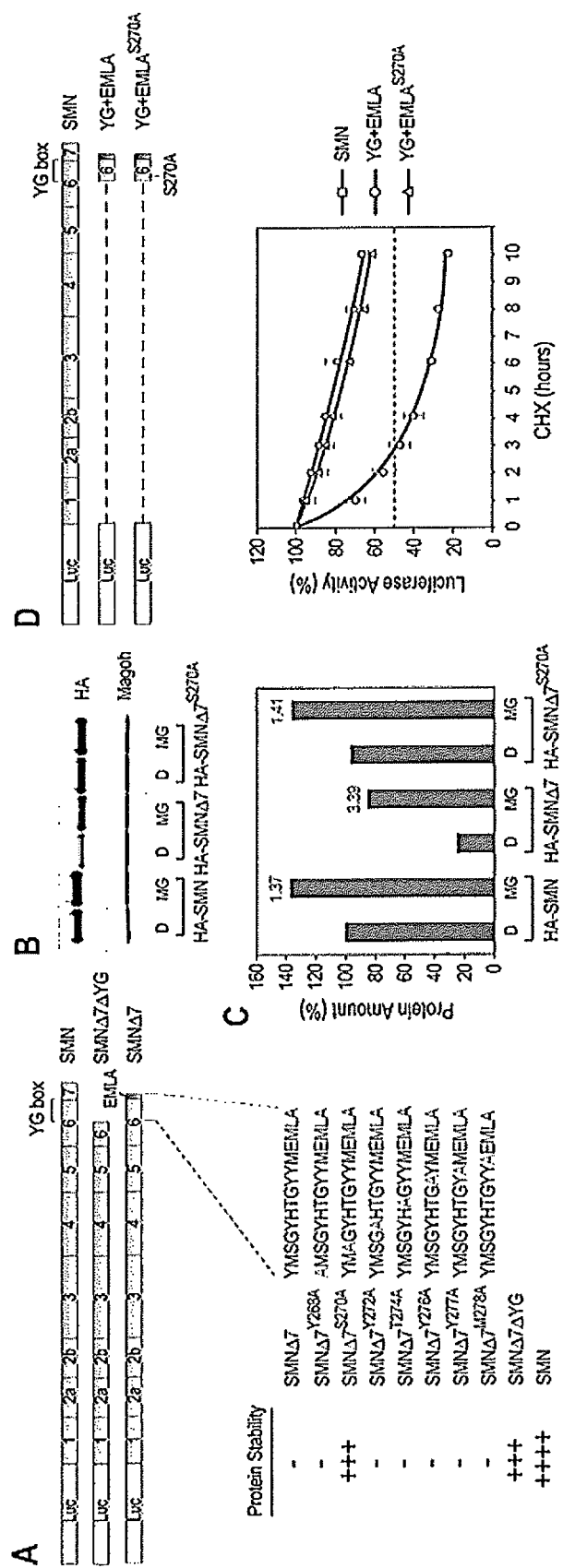
FIG. 3, comprising

To identify specific residues in the SMN07-DEG that are important for its activity, mutagenesis of the YG box was performed wherein every second residue was converted to alanine in the context of full-length SMNΔ7 and determined the half-life of each in 293T cells. Of seven mutations tested, S270A produced the most striking effect, reversing the destabilizing activity of the SMNΔ7-DEG (FIG. 3A). To confirm that S270A stabilizes SMNΔ7, HA-tagged proteins SMN, SMNΔ7, and SMNΔ7$^{s270A}$ were expressed in 293T cells for 24 hours and then treated with the proteasome inhibitor MG132 for 16 hours. The levels of the tagged SMN proteins were then monitored by Western blots using anti-HA antibody (FIG. 3B). As expected, the amount of SMNΔ7 without MG132 treatment was much lower than that of SMN. However, the amount of SMNΔ7$^{S270A}$ was similar to that of normal SMN indicating an almost complete restoration of stability by the S270A mutation. MG132 caused a dramatic increase in the amount of SMNΔ7 (3.4-fold) but only a moderate effect on SMN and SMNΔ7$^{S270A}$ (FIG. 3C). Therefore, the S270A mutation limits the proteasome degradation of SMNΔ7 and increases its stability very significantly.

The effect of S270A was further tested in the context of SMNΔ7-DEG alone. The S270A mutation strongly increased the stability of Luc-YG+EMLA to a level similar to that of SMN (FIG. 3D). These data indicate that the enhancement of stability of SMNΔ7 by the S270A mutation occurs through SMNΔ7-DEG.

Example 4

Functionality of SMNΔ7$^{S270A}$

To determine whether SMNΔ7$^{S270A}$ is a functional SMN protein, a previously established cell system, the S5 cell line, was used to investigate if SMNΔ7$^{S270A}$ could rescue the viability of SMN-depleted cells. The S5 cell line is derived from chicken DT40 cells, in which the endogenous chicken SMN gene is disrupted by homologous recombination and SMN protein is exogenously expressed from a cDNA under tetracycline-repressible promoter (Wang et al., 2001, J Biol Chem 276(13):9599-605), Upon depletion of SMN, S5 cell growth arrests at 72 hours and cell death occurs. It is therefore useful to assess the physiological functionality of SMN mutants in this cell system by monitoring cell viability after turning off SMN cDNA expression and simultaneously expressing exogenous SMN mutants of interest.

Figure 4:
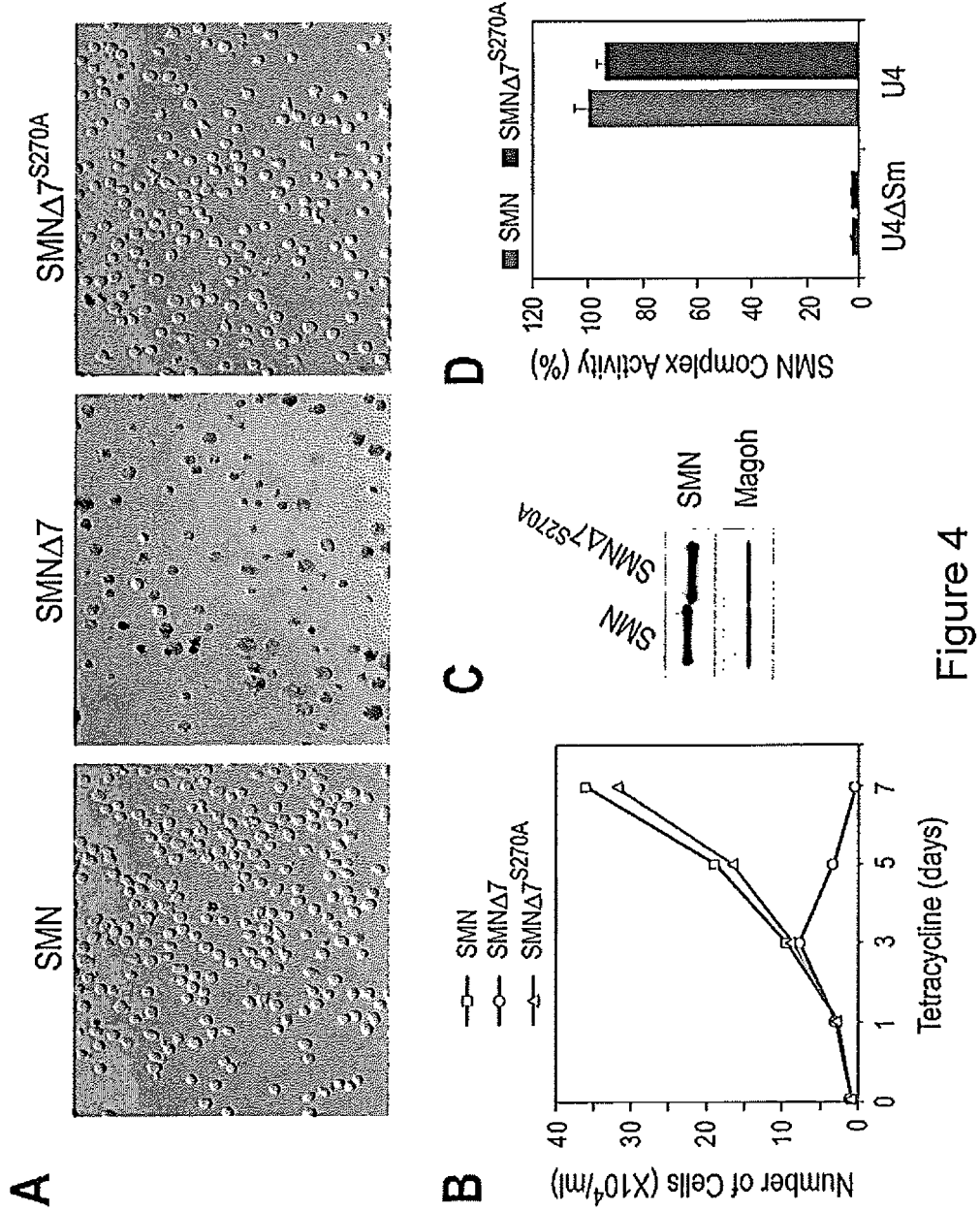
FIG. 4, comprising

To do so, recombinant retroviruses expressing SMN, SMNΔ7, or SMNΔ7$^{S270A}$ were constructed and used to transduce S5 cells. One week after repression of cSMN expression by tetracycline (1 μg/ml), there was a very clear difference in viable cell number among three samples (FIGS. 4A and 4B). While SMN rescued the viability of S5 cells, SMNΔ7 did not. Importantly, SMNΔ7$^{S270A}$ also rescued S5 cells to a similar extent as SMN. The two rescued cell lines expressed a similar level of SMN protein (FIG. 4C).

Example 5

Role of snRNP Assembly Defect with SMN Protein Functionality

The deficiency in functional SMN protein is directly correlated with snRNP assembly defects in cells of SMA patients (Wan et al., 2005, Mol Cell Biol 25(13):5543-51). Accordingly, the role of SMNΔ7$^{s270A}$ in snRNP assembly as a further measure of functionality was examined. Extracts from cells expressing SMN and SMNΔ7$^{S270A}$ were prepared and their snRNP assembly activity was measured. As shown in FIG. 4D, both cell lines showed similar activity. These data indicate that SMNΔ7$^{S270A}$ is a functional protein similar to normal SMN in S5 cells. The instability of SMNΔ7 conferred by SMNΔ7-DEG is a principal contributor to the deleterious phenotype of exon 7 skipping. However, S270A substitution in SMNΔ7 abrogates the degron activity, thereby restoring the function of SMN.

Several diverse classes of degrons that target proteins to various degradation pathways have been described. Most noted are N-degrons comprised of destabilizing N-terminal residues, C-terminal determinants containing relatively unstructured hydrophobic residues and phospho-degrons that are modulated by the phosphorylation status of their serine/threonine residues in response to cell signaling (Ravid et al., 2008, Nat Rev Mol Cell Biol 9(9):679-90; Parsell et al., 1990, Genes Dev 4(2):277-86). The short-lived tumor suppressor protein PTEN's stability depends on a 50-amino acid C-terminal tail that is phosphorylated at specific serine/threonine residues (Vazquez et al., 2000, Mol Cell Biol 20(14):5010-8). Interestingly, while many of the residues of the SMNΔ7-DEG could be substituted by alanines without loss of degron function, S270 is critical for the destabilizing function. It is therefore possible that S270 is phosphorylated and that this regulates the SMNΔ7-DEG activity. However, phosphorylation site analysis by NetPhos did not reveal strong candidate kinases for it. SMNΔ7-DEG has no obvious sequence similarity with the known degrons and, thus, represents a novel protein-destabilizing element. Protein database searches did not identify other known proteins containing highly similar sequences to SMNΔ7-DEG.

The reduced oligomerization efficiency of SMNΔ7 has been recently suggested to account for its instability (Burnett et al., 2009, Mol Cell Biol 29(5):1107-15). Indeed, intermolecular SMN oxidative crosslinking provided direct evidence that SMN is oligomeric in cells (Wan et al., 2008, Mol Cell 31(2):244-54). Oligomerization is likely to be important for SMN function and also to contribute to its stability. However, although SMN oligomerization correlated with its stability, this did not explain the intrinsic instability of SMNΔ7. The findings presented herein show that attachment of SMNΔ7-DEG to monomeric protein reporters (luciferase and GFP) triggered their rapid degradation, indicating that lack of oligomerization is not the major cause of SMNΔ7's instability. Loss of oligomerization capacity and other possible deficits as a result of deletion of the peptide encoded by exon 7 may result in a SMN protein that is functionally suboptimal. However, the detrimental effect of exon 7 skipping does not arise primarily from deletion of a functionally essential domain but from the creation of a positively acting and potent degron that causes severe deficiency of SMNΔ7 protein.

Given the ability of S270A mutation to restore SMNΔ7's stability and complement SMN loss of function, it is reasonable to predict that polymorphisms that inactivate SMNΔ7-DEG, such as at S270, would result in a milder SMA phenotype than the genotype predicts based on SMN2 copy number in SMN/-deleted individuals. Our finding with SMN07$^{S270A}$ indicates that SMNΔ7 is a functional SMN protein and that its stabilization could prevent or lessen SMA severity. We suggest that interfering with SMNΔ7-DEG activity could be an effective approach for mitigating its deficiency as a potential treatment for SMA. Although the inhibitor studies suggest that the degradation of SMNΔ7 likely occurs in the proteasome, general inhibition of proteasome activity would be very toxic, particularly in the long-term treatment that SMA would be expected to require. A targeted inhibition of the factors that mediate the SMNΔ7-DEG-dependent degradation should provide a more specific therapeutic approach, and their identification will be of great interest for SMA therapy.

SMA is thus the result of a fateful chain of events. Homozygous SMA1 deletion is a cause of SMA only because it exposes the splicing defect of SMN2. We argue that the splicing defect in SMN2 causes SMN deficiency because it fortuitously creates a degron. The degron is a key to SMA as it is the most direct cause of SMN deficiency, which then results in major perturbations in RNA metabolism.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. An isolated nucleic acid encoding a chimeric polypeptide comprising a degradation signal sequence and a target sequence, wherein the degradation signal sequence consists of SEQ ID NO. 3 or SEQ ID NO. 14.

2. An isolated nucleic acid consisting of SEQ ID NO. 3 or SEQ ID NO. 14, wherein said nucleic acid is operably linked to sequence of a vector.

* * * * *